(12) United States Patent
Nash

(10) Patent No.: US 9,645,120 B2
(45) Date of Patent: May 9, 2017

(54) METHOD AND APPARATUS FOR REDUCING NOISE TRANSMISSION THROUGH A WINDOW

(71) Applicant: Grant Nash, Melrose, MA (US)

(72) Inventor: Grant Nash, Melrose, MA (US)

( * ) Notice: Subject to any disclaimer, the term of this patent is extended or adjusted under 35 U.S.C. 154(b) by 0 days.

(21) Appl. No.: 14/846,488

(22) Filed: Sep. 4, 2015

(65) Prior Publication Data

US 2016/0071505 A1    Mar. 10, 2016

Related U.S. Application Data

(60) Provisional application No. 62/045,594, filed on Sep. 4, 2014.

(51) Int. Cl.
| | |
|---|---|
| *G01N 29/11* | (2006.01) |
| *E06B 5/20* | (2006.01) |
| *G10K 11/168* | (2006.01) |
| *E06B 3/67* | (2006.01) |

(52) U.S. Cl.
CPC .......... *G01N 29/11* (2013.01); *E06B 3/6707* (2013.01); *E06B 5/205* (2013.01); *G10K 11/168* (2013.01)

(58) Field of Classification Search
CPC .......... G10K 11/172; G10K 11/16; E04B 1/86
USPC ................................................. 181/207, 286
See application file for complete search history.

(56) References Cited

U.S. PATENT DOCUMENTS

| | | | |
|---|---|---|---|
| 2,379,194 A | 6/1945 | Shonts et al. | |
| 2,409,808 A | 10/1946 | Sowle | |
| 2,444,976 A | 7/1948 | Brown | |
| 2,473,616 A | 6/1949 | Stephenson | |

(Continued)

FOREIGN PATENT DOCUMENTS

| | | |
|---|---|---|
| EP | 0047725 | 3/1982 |
| FR | 889568 | 1/1943 |

(Continued)

*Primary Examiner* — Forrest M Phillips
(74) *Attorney, Agent, or Firm* — Pandiscio & Pandiscio

(57) ABSTRACT

Attenuators are introduced that offer quiet, enhanced sound quality for interior of enclosures than previous devices. An acoustical rating system for the levels of sound propagation through glass windows/windshields is introduced for the building and construction industry. Just as windows and insulation have an R-value to define the temperature energy efficiency of the interior of a room, an A-Rating™ system would define the acoustical energy efficiency of an enclosure space. In the summer, the higher the R-value, the less cool air that escapes a room through a window (and the less heat that penetrates into the interior), thus keeping the room cooler with less energy. Similarly, the higher the A-Rating™ of a window, the less noise that propagates through, maintaining lower levels of sound in the interior of an enclosure, creating a more harmonious, acoustically energy efficient room for enhanced health, preventing sleep interference, speech interference, and maintaining adequate levels of safety according to EPA and OSHA standards. The A-Rating™ system can help set standards for bearable and unbearable windows for a particular house, building, shopping store, restaurant, vehicle-cabin, fuselage cabin, locomotive/train/subway cabin, hotel, apartment, airport, library, museum, or any other enclosure, for a particular area or jurisdiction.

27 Claims, 17 Drawing Sheets

(56) References Cited

U.S. PATENT DOCUMENTS

| | | | |
|---|---|---|---|
| 2,912,724 | A | 11/1959 | Wilkes |
| 3,191,240 | A | 6/1965 | Slaman et al. |
| 3,343,317 | A | 9/1967 | Cripe |
| 3,429,530 | A | 2/1969 | Hertel |
| 3,553,913 | A | 1/1971 | Eisenberg |
| 3,953,630 | A | 4/1976 | Roberts et al. |
| 4,114,342 | A | 9/1978 | Okawa |
| 4,316,404 | A | 2/1982 | Medlin |
| 4,333,292 | A | 6/1982 | Musgrave |
| 4,456,335 | A | 6/1984 | Mumford |
| 4,460,314 | A | 7/1984 | Fuller |
| 4,622,249 | A | 11/1986 | Bowser |
| 4,776,763 | A | 10/1988 | Light |
| 4,829,729 | A | 5/1989 | Derner et al. |
| 4,932,608 | A | 6/1990 | Heidish et al. |
| 4,941,302 | A | 7/1990 | Barry |
| 5,005,557 | A | 4/1991 | Bachli |
| 5,009,218 | A | 4/1991 | Bachli |
| 5,119,608 | A | 6/1992 | Glover et al. |
| 5,120,584 | A | 6/1992 | Ohlenforst et al. |
| 5,154,953 | A | 10/1992 | De Moncuit et al. |
| 5,169,694 | A | 12/1992 | Endo et al. |
| 5,227,206 | A | 7/1993 | Bachli |
| 5,232,344 | A | 8/1993 | El-aini |
| 5,255,473 | A | 10/1993 | Kaspar et al. |
| 2,713,581 | A | 12/1993 | Irish |
| 5,343,619 | A | 9/1994 | Lardellier |
| 5,407,321 | A | 4/1995 | Rimkunas et al. |
| 5,584,662 | A | 12/1996 | Mannava et al. |
| 5,636,484 | A | 6/1997 | DeBlock |
| 5,732,517 | A | 3/1998 | Milikovsky |
| 5,766,755 | A | 6/1998 | Chaussade et al. |
| 5,820,343 | A | 10/1998 | Kraft et al. |
| 5,820,348 | A | 10/1998 | Fricke |
| 5,846,057 | A | 12/1998 | Ferrigno et al. |
| 6,155,789 | A | 12/2000 | Mannava et al. |
| 6,199,933 | B1 | 3/2001 | Gielda |
| 6,203,269 | B1 | 3/2001 | Lorber et al. |
| 6,224,339 | B1 | 5/2001 | Rhodes et al. |
| 6,224,341 | B1 | 5/2001 | Fricke |
| 6,238,187 | B1 | 5/2001 | Dulaney et al. |
| 6,260,317 | B1 | 7/2001 | Fisher |
| 6,328,532 | B1 | 12/2001 | Hahnle |
| 6,514,040 | B2 | 2/2003 | Lewis et al. |
| 6,787,204 | B2 | 9/2004 | Chaussade et al. |
| 6,793,990 | B1 | 9/2004 | Sakaguchi et al. |
| 6,802,162 | B1 | 10/2004 | Fisher |
| 6,830,791 | B1 | 12/2004 | Misonou et al. |
| 6,886,297 | B1 | 5/2005 | Crandell |
| 6,905,094 | B2 | 6/2005 | Dazet et al. |
| 7,249,653 | B2 * | 7/2007 | Sheng ................. E04B 1/86 181/207 |
| 7,266,930 | B1 | 9/2007 | Fisher |
| 7,395,898 | B2 * | 7/2008 | Yang ................. G10K 11/172 181/286 |
| 7,552,896 | B2 | 6/2009 | Coak |
| 7,721,844 | B1 | 5/2010 | Lewis et al. |
| 7,763,334 | B2 | 7/2010 | Berkowitz |
| 7,845,142 | B2 | 12/2010 | Theios |
| 7,856,770 | B2 | 12/2010 | Grassmuck et al. |
| 8,033,505 | B2 | 10/2011 | Wieting |
| 8,082,707 | B1 | 12/2011 | Lewis et al. |
| 8,439,154 | B1 | 5/2013 | Lewis et al. |
| 8,550,206 | B2 * | 10/2013 | Keady ................. H04R 25/656 181/135 |
| 8,616,330 | B1 * | 12/2013 | McKnight ............ G10K 11/16 181/207 |
| 8,857,563 | B1 * | 10/2014 | Chang ................. H03H 9/25 181/286 |
| 8,857,564 | B2 * | 10/2014 | Ma ................. G10K 11/18 181/284 |
| 8,869,933 | B1 * | 10/2014 | McKnight ............ G10K 11/172 181/207 |
| 9,270,253 | B2 * | 2/2016 | Chang ................. G10K 11/172 |
| 2003/0234322 | A1 | 12/2003 | Bladt et al. |
| 2004/0238690 | A1 | 12/2004 | Wood et al. |
| 2006/0118676 | A1 | 6/2006 | Novak et al. |
| 2007/0069080 | A1 | 3/2007 | Rassaian et al. |
| 2007/0148379 | A1 | 6/2007 | Theias et al. |
| 2012/0094084 | A1 * | 4/2012 | Fisher ................. B32B 17/10036 428/174 |
| 2016/0027427 | A1 * | 1/2016 | Yang ................. G10K 11/175 181/286 |

FOREIGN PATENT DOCUMENTS

| | | |
|---|---|---|
| GB | 2026622 | 2/1980 |
| JP | S61181794 | 8/1986 |

* cited by examiner

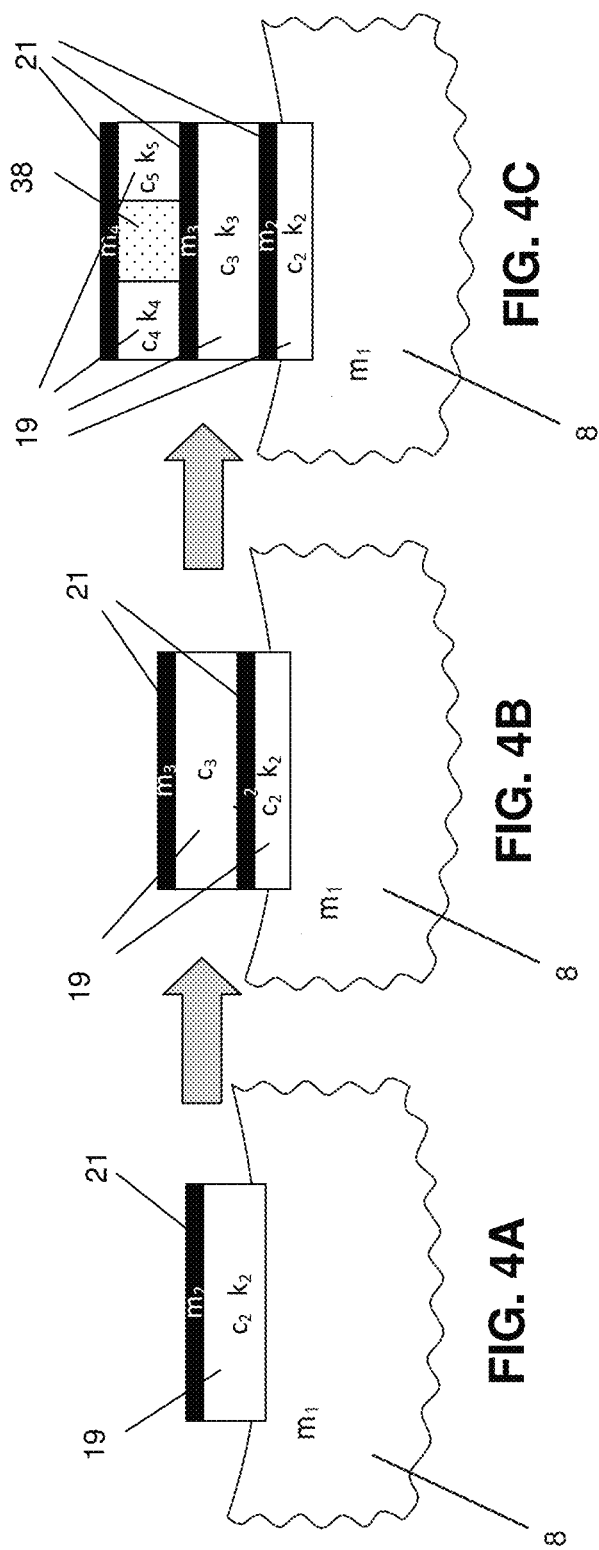

Armored Van

Armored Truck

Piper Cherokee Six 260

Piper 140

Top View

Side View

Top View

Side View

Top View

Side View

METHOD AND APPARATUS FOR REDUCING NOISE TRANSMISSION THROUGH A WINDOW

REFERENCE TO PENDING PRIOR PATENT APPLICATION

This patent application claims benefit of prior U.S. Provisional Patent Application Ser. No. 62/045,594, filed Sep. 4, 2014 by Grant Nash for BEARABLEGLASS/WINDOW/WINDSHIELD™ (BEARABLES™) FOR REDUCING NOISE LEVELS IN INTERIOR OF BUILDINGS, HOUSES, SHOPPING STORES, RESTAURANTS, VEHICLE-CABINS, FUSELAGE CABINS, LOCOMOTIVE/TRAIN/SUBWAY CABINS, HOTELS, APARTMENTS, AIRPORTS, LIBRARIES, MUSEUMS, AND ANY OTHER TYPE OF ENCLOSURE, WITH AN A-RATING™ AND S-RATING™ FOR BUILDING/CONSTRUCTION CODES, which patent application is hereby incorporated herein by reference.

FIELD OF THE INVENTION

The present invention relates to methods and apparatus for the reduction of noise transmission through glass (including but not limited to windows and windshields) and into interior spaces (including but not limited to houses, vehicle cabins, fuselages, locomotive cabins and train coaches, boat cabins, buildings, rooms, spaces, apartments, hotels, airports, and other interior spaces having windows). For the purposes of the present invention, the term "window" is intended to mean, where the context so admits, windows, windshields, glass-containing doors and ceilings and skylights, transparent or translucent panels, and the like. And for the purposes of the present invention, the term "glass" is intended to mean, where the context so admits, glass, plexiglass, transparent or translucent plastics, and the like.

The present invention also relates to the creation and use of rating systems for evaluating the propagation of sound through glass (e.g., an A-Rating™ and an S-Rating™), including but not limited to windows and windshields.

The A-Rating™ is for low frequency sound (preferably from 20 to 200 Hz) just inside the glass window/windshield. The S-Rating™ is for broadband frequency sound (preferably throughout the entire hearing range of 20 to 20,000 Hz).

Typically, low frequency sound dominates noise propagation into interior spaces and is more difficult and costly to reduce. This invention focuses primarily on reducing low-frequency noise levels, and thus, increasing the A-Rating™ of the glass.

BACKGROUND OF THE INVENTION

Noise transmission into the interior of buildings, houses, vehicle cabins, fuselages, and other interior spaces has existed throughout human history. Reducing noise transmission for better sound quality helps enhance health, prevent sleep interference and prevent speech interference. Reducing noise transmission into enclosures can also be important for protecting people from hearing loss and complying with standards prescribed by regulators, e.g., the Environmental Protection Agency (EPA) and the Occupational Safety and Health Administration (OSHA).

Previous noise reduction techniques for glass, including but not limited to windows and windshields, have predominantly consisted of reducing the noise by a limited number of decibels over the entire hearing range (20-20,000 Hz). However, this approach typically affords little reduction in the overall noise levels, let alone low frequency noise from 20 to 200 Hz.

As seen in FIGS. 1A and 1B, previous noise reduction techniques have also included thickening of the glass window 1 (typically contained within a windowsill 3) to stiffen the window and reduce high frequency noise transmission. This can be costly, driving up the price to manufacture the glass.

Looking next at FIG. 1C, other techniques have included the introduction of air gaps within the window during the manufacturing of the glass, thereby providing double-pane windows (with a gap 39 between the two panes), whereby to mitigate high frequency vibration and thus reduce high frequency structure-borne noise. Some have even put a transparent material 40 (FIG. 1D) into the air gap to help reduce noise transmission.

Moreover, the building and construction industry utilizes R-values to rate the temperature energy efficiency of a window in relation to an interior space. The higher the R-value of the window, the higher the energy efficiency of the window. In the summer, a window with a high R-value allows less warm air to penetrate into the interior of the structure and thus helps to sustain a cool interior temperature for better energy efficiency. Similarly, in the winter, a high R-value allows less warm air to escape from a house or building, thereby helping to sustain a warm temperature for better energy efficiency.

Some glass (e.g., windows and windshields) can be modally sparse and some can be modally dense. Modally dense glass elements can typically be defined as elements that vibrate with modes (or resonant frequencies) separated by less than 40 Hz in a low frequency bandwidth between 20 and 200 Hz. In modally sparse glass elements, only one resonant frequency may be present, or two (or only a few) resonant frequencies may be present. The vibration at these resonant peaks is reduced and thus the majority of the energy is attenuated. Mass, stiffness, and damping is applied to these few peaks and noise transmission mitigated. For modally dense glass elements, many different mass, spring or damping systems can be utilized to reduce overall energy across a frequency spectrum (e.g., 20 to 200 Hz for low frequency systems and 20 to 20,000 Hz for systems of the full human hearing range).

Many types of noise can awaken people at night, distract from daily life, and affect health. For houses near busy streets, low frequency engine noise from cars, motorcycles, construction vehicles, etc. can penetrate into the interior of enclosures and awaken residents, especially when engines are revved late at night. For buildings near airports, noise from aircraft, typically in the form of blade-passage-frequency (BPF) noise, can transmit into the interior of the building. Construction next to a restaurant can make it difficult to maintain a conversation inside. Similarly, when a subway or train comes to a screeching halt, it can be nearly impossible to maintain a conversation in the interior of the car because of the brake noise. Moreover, when one is inside a vehicle and an adjacent automobile is blaring music with high bass, it can distract from the acoustics of the environment.

SUMMARY OF THE INVENTION

The present invention helps to reduce noise transmission through glass (e.g., windows and windshields) utilizing mass, stiffness, and damping characteristics (sometimes hereinafter referred to as a "Degree-of-Freedom system" or "DOF system") in order to obtain desired sound levels in the interior of houses, buildings, vehicle cabins, fuselages, locomotives, train coaches, subways, conference rooms, libraries, hotels, laboratories, and other similar interiors. As mentioned above, previous methods have predominantly concentrated on utilizing damping alone, or stiffness alone, to improve sound quality. What is unique about this invention is that glass (e.g., windows and windshields) is attenuated by a novel attenuator taking into account all three of mass, stiffness, and damping. If a particular window has sharp resonant peaks, with little damping, the novel attenuator can have little damping and concentrate mainly on the mass and stiffness to cancel the energy at particular resonances.

With the present invention, the novel attenuator effectively creates an "anti-resonance" at an appropriate frequency attenuation bandwidth to cancel an undesirable resonant peak sound transmission.

In other words, the novel attenuator of the present invention utilizes the elastic element of the attenuator, and the mass element of the attenuator, to provide natural mode(s) of vibration (in essence, "anti-resonance") that counteracts the undesirable resonant peak(s) in the window. With a 1-DOF attenuator, the attenuator creates one natural mode (i.e., one frequency attenuation bandwidth) that counteracts one undesirable resonant peak in the window; with a 2-DOF attenuator, the attenuator creates two natural modes (i.e., two frequency attenuation bandwidths) that counteract two resonant peaks in the window, etc.

To those familiar with the art, the amount of damping for a peak can be described with a Q-factor. The higher the Q-factor, the less the damping in the peak (i.e., width of the peak is narrower). Similarly, the lower the Q-factor, the higher the damping in the peak (i.e., width of the peak is wider). However, the uniqueness of this invention (sometimes referred to herein as a novel attenuator) is that the majority of the energy cancellation concentrates on the resonant peaks, which is where the majority of the unhealthy and/or undesirable noise is concentrated. Previous systems, which concentrate on damping, reduce the majority of energy at frequencies outside the resonant peaks. Thus, these previous systems reduce sound which is not bothersome to the human health condition rather than attenuating noise that can be detrimental to one's health.

A damping method or air-gap method can reduce some energy at a resonant peak, but it is very little compared to a system which concentrates on reducing energy at particular resonant peak(s) (i.e., the approach used in the present invention). In a system that concentrates on reducing energy at a particular resonant peak (i.e., the approach used in the present invention), there is typically an order of magnitude or more in sound reduction (which is a massive amount of energy reduction compared to a conventional method).

For instance, the plot in FIG. 7 shows a Power Spectrum Density (PSD) plot of a windshield with and without a novel attenuator formed in accordance with the present invention. In FIG. 7, the frequency response of each system shown (i.e., a window with and without a novel attenuator formed in accordance with the present invention) is utilizing a transfer function of the output over the input so the decibel output is a ratio related to the power. So, although the acoustic attenuation of the resonant peak in the 80 to 90 Hz region is about 10 dB (12 dB at 83 Hz, 10 dB at 87 Hz), it should be noted that this means that the glass window attenuated with the novel attenuator of the present invention transmits 8 times less power than the unattenuated glass. This power reduction is impractical to achieve with conventional damping window attenuation.

In another aspect of the present invention, there is provided an A-Rating™ system, wherein attenuated and unattenuated windows can be defined and/or rated for the building and construction industry. Houses, lodging establishments, buildings, etc. could be subjected to construction and/or other codes which would recommend or require that the structures include windows with an appropriate A-Rating™ so as to provide for appropriate and/or desirable interior sound levels.

The majority of unwanted noise occurs in the low frequency region (e.g. 20 to 200 Hz). This noise can be more difficult and costly to attenuate, so finding a cost-effective means to attenuate noise in this frequency region would be beneficial. The present invention concentrates on energy levels in this frequency range, however, the present invention also contemplates providing noise attenuation for the entire human hearing range of 20 to 20,000 Hz for an interior space.

Accordingly, an alternative S-Rating™ system is contemplated for defining and rating noise attenuation for a full human hearing frequency spectrum. Table 1 (see below) shows an A-Rating™ scale as well as an S-Rating™ scale. Depending on the applicable local, regional, state, or federal regulation(s), attenuated and unattenuated levels/ratings can be established for a particular structure in a particular area for use by the construction industry.

By way of example, in an area where noise levels are particularly high, such as near an airport, airport windows or building windows nearby might need to be equipped with a window of at least an A-8 rating (i.e., a window having the "A-8" characteristics shown in Table 1). In a quieter community, with little noise, a window with an A-3 rating (i.e., a window having the "A-3" characteristics shown in Table 1) might only be needed. For a house on a busy street, with high volumes of vehicle traffic, a window with an A-6 rating (i.e., a window having the "A-6" characteristics shown in Table 1) might be necessary.

In addition, although it would be rare, there might be a need to enhance and/or amplify sound into a particular enclosure. The regulatory agencies could set the attenuated/unattenuated limits required for a particular area in accordance with the A-Rating™ and S-Rating™ scales of the present invention.

Decibel reduction is based on a test in which a microphone or multiple microphones are placed approximately 6 inches from a window. When three microphones are utilized, one should be placed towards the top of the window, one towards the middle of the window, and one towards the bottom of the window. An average sound pressure level ("SPL") is obtained, based on the data obtained by the three microphones.

Various acoustical sources can be applied during testing. Universally, white noise at 90 dB could be directed at the window and microphone levels obtained on the other side of the window while installed with baffle-like boundary conditions for the setup to ensure the acoustical energy is being measured for energy transmitted through the window.

The testing could be completed and the rating assigned before shipping and installing the window (with attenuator) in a house, building, structure, etc. If a particular area has a certain "type" of noise (e.g., noise from particular sources that generate energy at particular frequencies), that particular "type" of noise could be applied to the window (with attenuator) during testing. By way of example but not limitation, for windows to be installed in proximity to a particular busy street that has engine noise with typical resonant peaks at 100 Hz, the novel attenuator could be constructed so as to maximize energy reduction at that particular frequency.

In the foregoing scenario, the majority of the attenuation in a 20 to 200 Hz region would be concentrated around 60 Hz. The application of the A-Rating™ scale would still require taking the average reduction over the frequency range. By way of example but not limitation, if the resonant peak was reduced 9 dB, but the overall average reduction for the frequency range was 6 dB, then the window (with attenuator) would have an A-5 rating. In another example, if the resonant peak was reduced 9 dB and the overall average reduction for the frequency range was 9 dB, then the window (with attenuator) would have an A-6 rating. Another example could be if a building is by an airport and is subjected to a typical BPF of around 85 Hz, then the novel attenuator would be constructed so as to maximize energy reduction at that particular frequency.

TABLE 1

Acoustical Ratings for Windows for Building and Construction Industry

| A-rating™ | A-rating™ SPL Reduction* (low frequency acoustical energy from 20-200 Hz) | S-rating™ | S-rating™ SPL Reduction* (acoustical energy in frequency spectrum of entire human hearing range of 20-20,000 Hz) |
|---|---|---|---|
| | (dB) | | (dB) |
| A-1 | +6 and Above | S-1 | +6 and Above |
| A-2 | +3 | S-2 | +3 |
| A-3 | 0 | S-3 | 0 |
| A-4 | −3 | S-4 | −3 |
| A-5 | −6 | S-5 | −6 |
| A-6 | −9 | S-6 | −9 |
| A-7 | −12 | S-7 | −12 |
| A-8 | −15 | S-8 | −15 |
| A-9 | −18 | S-9 | −18 |
| A-10 | −21 | S-10 | −21 |
| A-11 | −24 | S-11 | −24 |
| A-12 | −27 and Below | S-12 | −27 and Below |

*For multiple microphones, average SPL over frequency range

In the case of glass (e.g., window and windshield) manufacturing, one or more novel attenuators may be imbedded in the window, or affixed to the glass (in one form of the invention, with a covering over the top of the attenuator to prevent the attenuator from being tampered with). In the case where the attenuator(s) is/are affixed to a window, the attenuator(s) can be adhered, fixed, fastened, etc. as necessary or appropriate.

The attenuator(s) can be in various shapes, sizes, designs, etc. For aesthetic purposes, the attenuator(s) could be in the shape of various animals, objects, landmarks, structures, people, scenes, etc. to provide a decorative aspect to the window. Furthermore, the attenuators could be enhanced with various colors, artwork, painting, etc. to enhance their aesthetic appeal.

In one embodiment of the present invention, and looking now at FIGS. 3, 4B, 4C, 5A and 5B, there is provided a 2-Degree-of-Freedom (2-DOF) novel attenuator used in connection with an exemplary aircraft windshield (note that FIG. 4A shows a novel 1-DOF attenuator). In this embodiment, the 2-Degree-of-Freedom (2-DOF) novel attenuator is configured to attenuate the BPF noise penetrating into the fuselage at approximately 87 Hz that can coincide with a 80-90 Hz mode in the windshield. The windshield of this embodiment is also configured to attenuate sound propagating into the interior of the fuselage via another mode in the windshield (200 Hz) that coincides closest to the second harmonic of the BPF (174 Hz). A schematic model of the 2-DOF novel attenuator is shown in FIG. 5A, and an example of a 2-DOF novel attenuator is shown in FIG. 5B.

In practice, the novel attenuators (or neutralizers) of the 2-DOF device are preferably configured to have a shape compatible with the windshield of a particular vehicle or apparatus, e.g., windshields utilized with armored trucks, Piper 140 airplanes, and Piper Cherokee Six 260 airplanes. In this particular exemplary embodiment, the novel attenuator eliminates the energy transmitting into the interior of the fuselage at the BPF (87 Hz) and 200 Hz peaks.

In another embodiment of the present invention, and looking now at FIGS. 8A, 8B, 9A, 9B, 10, a 3-DOF novel attenuator can be utilized to eliminate energy at three resonant peaks where noise transmits through the window into the interior of a house. FIG. 10 shows a plot of the energy propagating through the window showing the acoustical energy is eliminated at the particular frequency peaks targeted. In further embodiments of a 3-DOF novel attenuator, and looking now at FIGS. 12, 13A, 13B, 14A, and 14B, various additional types of novel 3-DOF attenuators shown. In these embodiments, targeted resonant peaks are attenuated by attenuators comprising mass, elastic, and stiffness elements.

In addition, multi-DOF attenuators having more than 3 DOFs can be designed. By way of example but not limitation, in the embodiment shown in FIGS. 15A and 15B, four (or more) peaks are targeted to reduce noise transmitting through the window into the interior of an enclosure for a particular frequency range, as shown in FIGS. 16A and 16B. It should be appreciated that novel attenuators having 5-DOF, 6-DOF, 7-DOF, etc. can be formed in accordance with the present invention.

The aforementioned embodiments may be formed by boring out chambers in the elastic layer of the novel attenuators (i.e., FIGS. 12, 13A, 13B, 14A, and 14B show 3-DOF attenuators, and FIGS. 15A and 15B show 4-DOF attenuators). The elastic layer can be filled with rubber, gel, foam or other substances exhibiting the property of flowability. Varying the composition of the elastic layer (i.e., by providing different inserts into the elastic layer), among other things, provides for the ability to attenuate multiple peaks instead of just one peak.

In another embodiment of the multiple DOF attenuator, the ability of an attenuator to shift frequencies in order to tune to a particular resonant peak is possible by varying the stiffness element of the attenuator. In an embodiment with shifting stiffness characteristics of the invention, bores or chambers may be formed in the elastic layer of the attenuator and sealed. These bores or chambers can be filled with air or another gaseous mixture. The attenuator may also be provided with knobs or other valves to control closures configured to open and close so as to allow the fluid to flow from one chamber to another, or from a reservoir chamber to another chamber. By varying the amount of fluid in the chambers, the attenuator may be tuned to adjust and match the resonant frequency range of a window or windshield, thereby creating an anti-resonance to help maximize attenuation at particular frequency ranges. This can allow customization and targeting of various kinds of noise resonating from a window or windshield and propagating into the interior of a particular house, building, vehicle, etc.

In still another embodiment of the present invention, the chambers can be filled with a fluid containing iron particles and a magnetic field applied to the chamber. See FIGS. 14A, 14B, 15A and 15B. By increasing the strength of the magnetic field applied to the chamber, the fluid becomes significantly less flowable, thereby increasing the stiffness of the individual filled chamber (which acts as something of a column). In this way, the stiffness of the filled chamber (column) can be varied, which results in the tunability of the attenuator to neutralize the resonant peak for the window and thus reducing noise propagating into the interior of the house or building. The novel attenuator would have settings to increase or decrease the current and thus the stiffness of the chamber of the novel attenuator.

In one preferred form of the invention, there is provided an attenuator for reducing sound transmission through a structure, said attenuator comprising:
at least one elastic body characterized by a damping attribute and a stiffness attribute; and
at least one mass secured to said at least one elastic body;
wherein said at least one elastic body is configured to be secured to said structure intermediate said structure and said at least one mass;
and further wherein said damping attribute of said at least one elastic body, said stiffness attribute of said at least one elastic body and said at least one mass are selected so as to provide at least one frequency attenuation bandwidth focused on a single resonant peak of sound transmission through a structure.

In another preferred form of the invention, there is provided a system for reducing sound transmission through a structure, said system comprising:
a structure; and
an attenuator attached to said structure, said attenuator comprising:
at least one elastic body characterized by a damping attribute and a stiffness attribute; and
at least one mass secured to said at least one elastic body;
wherein said at least one elastic body is configured to be secured to said structure intermediate said structure and said at least one mass;
and further wherein said damping attribute of said at least one elastic body, said stiffness attribute of said at least one elastic body and said at least one mass are selected so as to provide at least one frequency attenuation bandwidth focused on a single resonant peak of sound transmission through a structure.

In another preferred form of the invention, there is provided a method for reducing sound transmission through a structure, said method comprising:
attaching an attenuator to the structure, said attenuator comprising:
at least one elastic body characterized by a damping attribute and a stiffness attribute; and
at least one mass secured to said at least one elastic body;
wherein said at least one elastic body is configured to be secured to said structure intermediate said structure and said at least one mass;
and further wherein said damping attribute of said at least one elastic body, said stiffness attribute of said at least one elastic body and said at least one mass are selected so as to provide at least one frequency attenuation bandwidth focused on a single resonant peak of sound transmission through a structure.

In another preferred form of the invention, there is provided an acoustic rating system for windows based on noise amplitude and frequency.

In another preferred form of the invention, there is provided a method for characterizing a window, the method comprising:
testing the sound transmission of a window; and
characterizing the window in the context of an acoustic rating system based on noise amplitude and frequency.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 4A, 4B and 4C are schematic diagrams showing 1-DOF, 2-DOF, and 3-DOF attenuators;

FIGS. 13A and 13B show further enhancements of the novel attenuator depicted in FIG. 12, in which the chambers in the elastic layer are filled with air or a gaseous mixture contained in a bag such as a balloon—the pressure in each bag can be increased by actuating rubber bulbs on the side of the attenuator in order to adjust the buoyancy of the mass disposed on the filled chamber (column) of air/gaseous-mixture, wherein FIG. 13A is a top view of the attenuator and FIG. 13B is a side view of the attenuator—FIGS. 13A and 13B also show three valves below the rubber bulbs which can be opened to slowly release air from the chambers, wherein adding air to, or releasing air from, the chambers can adjust the peaks of attenuation of the attenuator, thereby allowing a user to target various resonant peaks of noise that can propagate through a window for a particular environment;

—FIG. 16A shows multiple resonant peaks of low frequency noise (20 to 200 Hz) propagating into the interior of a house, building, enclosure or the like, which can be eliminated by use of novel attenuator(s), and FIG. 16B shows multiple resonant peaks for a broader band frequency spectrum for the entire human hearing range (20 to 20,000 Hz) that can be eliminated by novel attenuator(s).

DETAILED DESCRIPTION OF THE PREFERRED EMBODIMENTS

The novel attenuator of the present invention reduces noise transmission into the interior of buildings, houses, restaurants, vehicle cabins, fuselages, and other enclosures, which is an issue that has been around throughout human history. The lower sound levels in interior spaces helps to enhance health, prevent sleep interference, prevent speech interference, and helps to maintain safe sound levels that may be prescribed by EPA and OSHA standards. These are just a few of the key incentives for reducing noise pollution in interior spaces.

The novel attenuator of the present invention attenuates resonant peaks that are vibrating the glass window/windshield and propagating structure-borne noise into an interior of an enclosure.

Figure 1A:
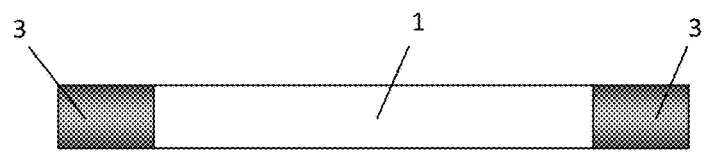
FIG. 1A is a top view of a typical prior art window.
Figure 1B:
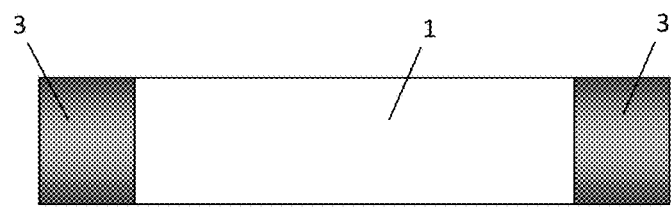
FIG. 1B is a top view of a prior art window where the glass is thickened.
Figure 1C:
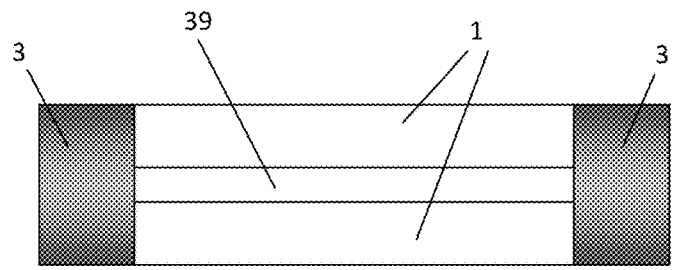
FIG. 1C is a top view of a prior art window where an air gap is provided between two panes of glass.
Figure 1D:
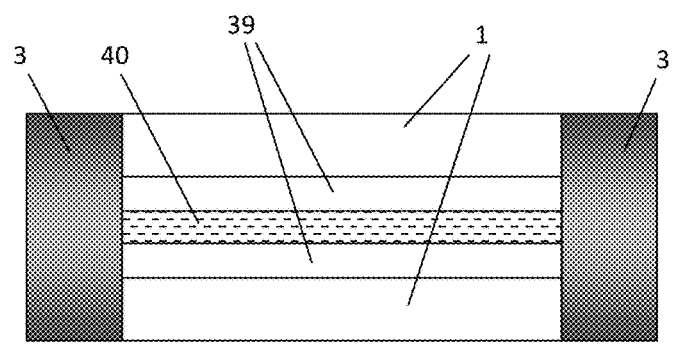
FIG. 1D is a top view of a prior art window where transparent material is provided between two air gaps and pieces of glass.
Figure 2D:
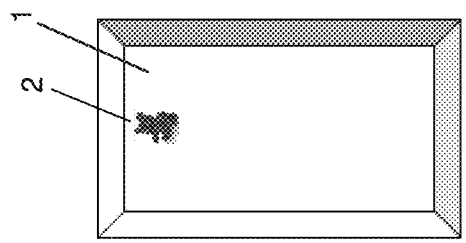
FIGS. 2A-2D show a few different types of window/attenuator systems formed in accordance with the present invention to reduce noise transmission into the interior of houses, buildings, shopping stores, apartments, hotels, restaurants, and any other enclosure interior.
Figure 2C:
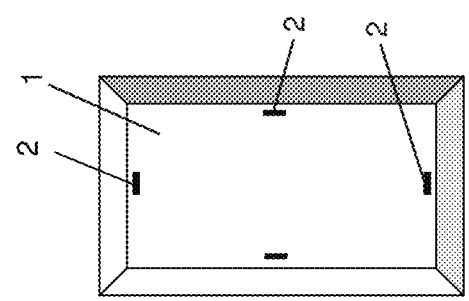
Figure 2B:
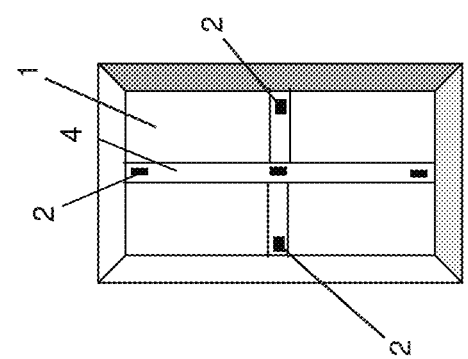
Figure 2A:
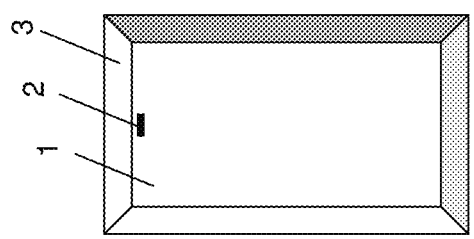

An example of a novel attenuator that reduces noise transmission into the interior of houses, buildings, shopping stores, restaurants, hotels, apartments, libraries, museums, and any other interior enclosure can be seen in FIG. 2A. Glass 1 has an outer windowsill 3 and a novel attenuator 2 formed in accordance with the present invention. FIG. 2B shows a typical window that has trim 4 in the middle, with the attenuators attached to trim 4. Multiple attenuators can be fastened, fixed, adhered, embedded into the surface, etc. of the window, as shown in FIG. 2C. Additional attenuator embodiments can include an attenuator mass that is decorative and enhances the aesthetics of a room, as shown in FIG. 2D.

Figure 3:
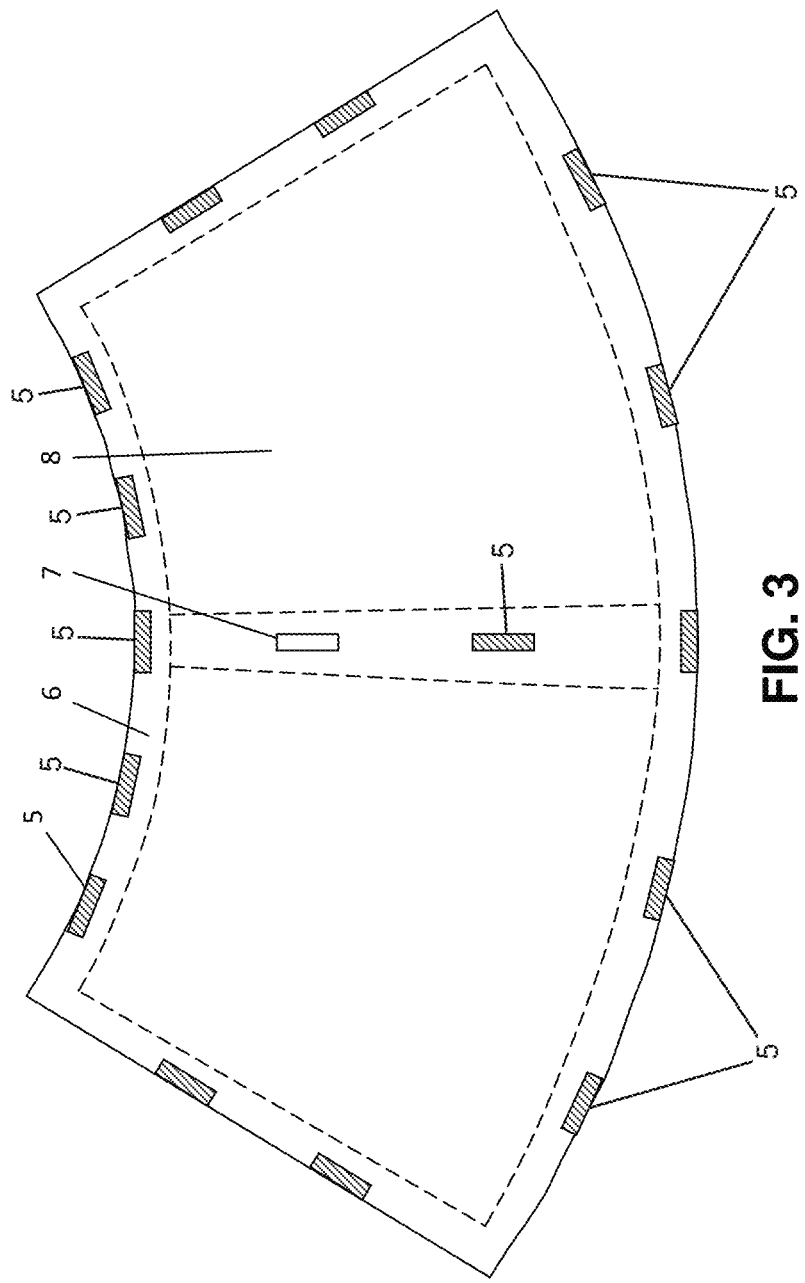
FIG. 3 is a schematic view showing attenuators formed in accordance with the present invention applied to a windshield so as to reduce noise transmission into the interior of an airplane fuselage.

An example of a novel attenuator system that reduces noise transmission into the interior of an airplane fuselage can be seen in FIG. 3. Noise from the 87 Hz BPF of the airplane propagates into the interior of the fuselage cabin. Previous research has found that the majority of noise for a single-propeller aircraft transmits through the windshield. The BPF happens to coincide with a 80-90 Hz windshield mode. Trim 6 around the edge of the windshield utilizes multiple attenuators 5 to cancel the vibration in the plexiglass windshield 8 in the 80-90 Hz region.

The windshield mode around 200 Hz also transmits sound energy into the cabin of the fuselage, although this sound energy is somewhat less than the fundamental BPF sound energy. This closest mode in the windshield to the second harmonic of the BPF was targeted as a second peak for noise attenuation (200 Hz).

In accordance with the present invention, 2-DOF attenuators have been designed to reduce noise transmission into the interior of the fuselage cabin at the two targeted frequencies. Attenuators 5 are adhered to trim 6 based on the design of windshields for armored trucks and other airplanes, including the Piper, as shown in FIGS. 6A-6D. Rearview mirror 7 (FIG. 3), attached to the windshield of the aircraft, ends up being on an anti-node for 80-90 Hz resonance and is left in place.

Figures 15A, 15B:
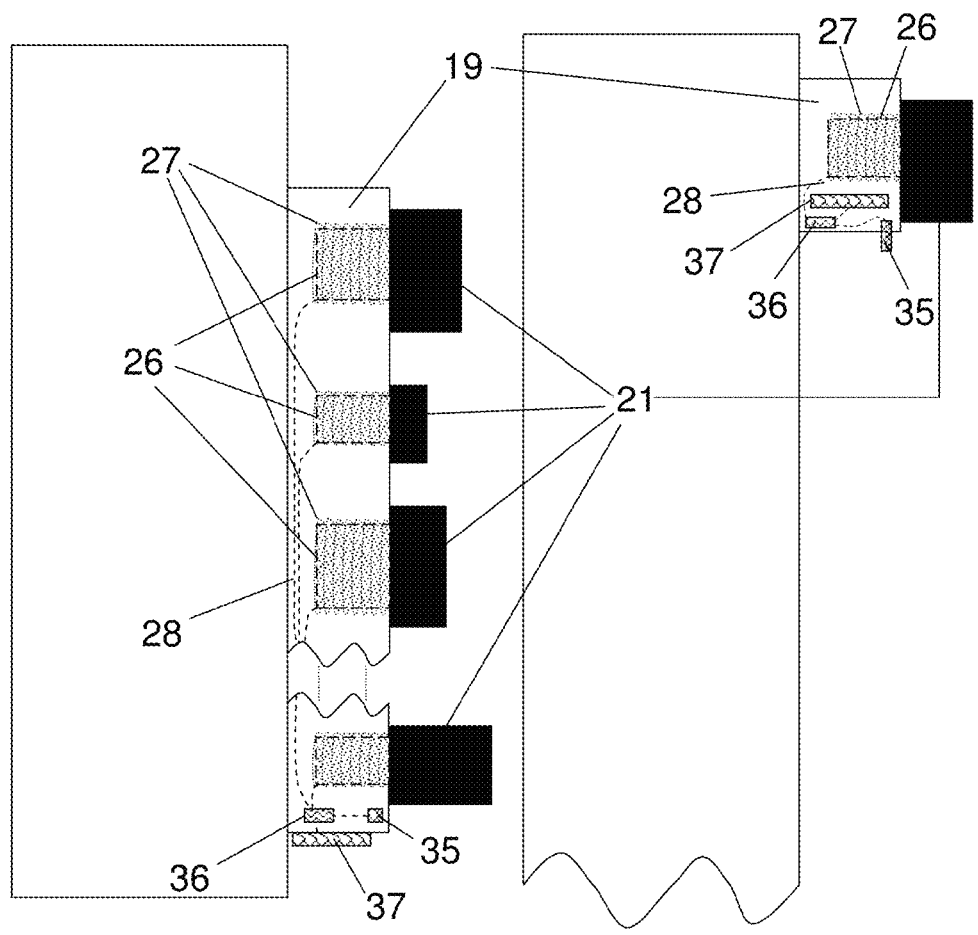
FIGS. 15A and 15B are schematic views showing a multi-DOF attenuator that contains an active sound control system, which can automatically adjust for troublesome resonant peaks of noise and tune attenuation peaks to cancel the noise—a microphone is utilized as a control feedback sensor for a Central Processing Unit (CPU), and a digital display with touchscreen controls can be utilized for manual adjustments as an optional feature.

Attenuators 5 are mass/spring/damping systems that can be tuned to a frequency of attenuation in order to target bothersome resonant peaks, utilizing Equation 1, which is derived from Newton's Second Law of Motion:

$$f_{attenuation} = \frac{(k/m)^{1/2}}{2\pi} \qquad \text{(Equation 1)}$$

where the k term in the equation represents the stiffness of the attenuator, the m term represents the mass of the attenuator, and the f term denotes the frequency of attenuation. Attenuators 5 can be a 1-DOF, 2-DOF, or 3-DOF (as shown in FIG. 4A-4C), or a 4-DOF (or more) system (as shown in FIGS. 15A and 15B).

Figure 5A:
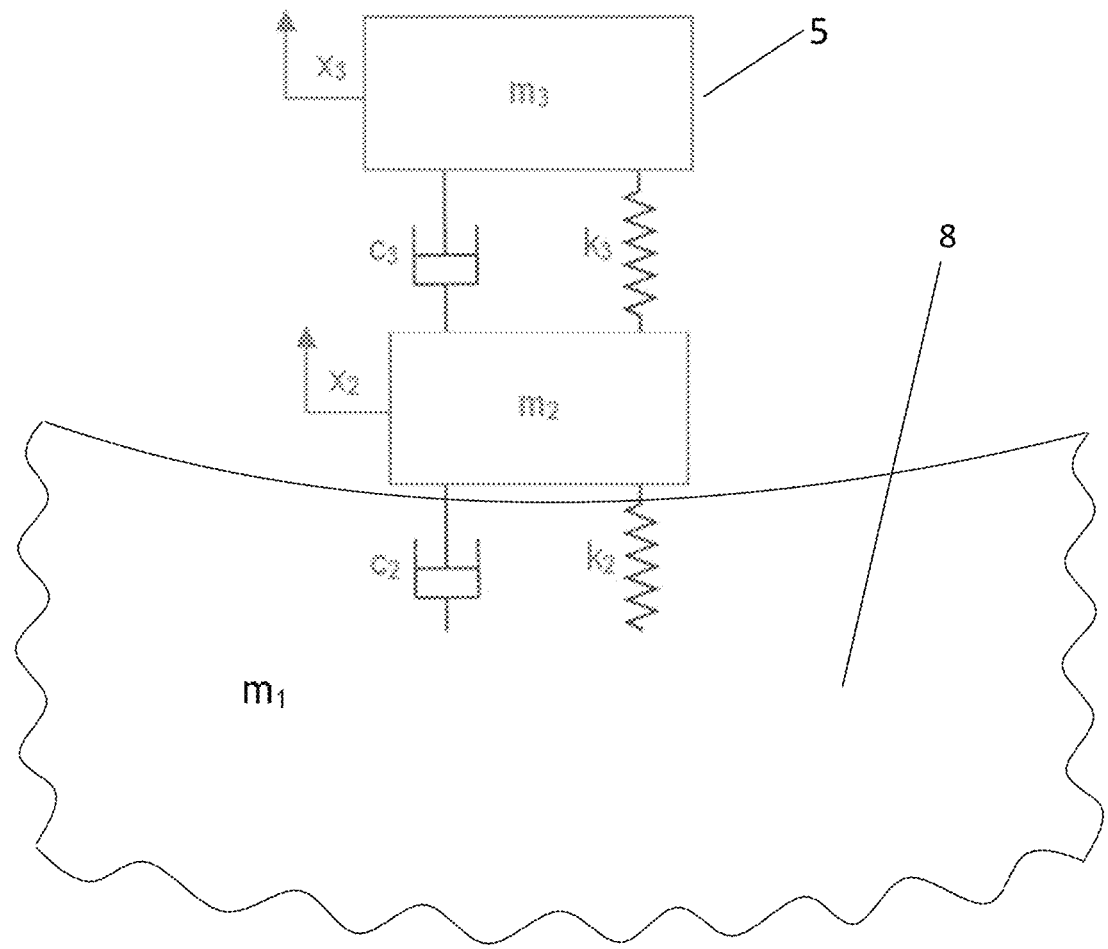
FIG. 5A is a schematic view illustrating a model of the 2-DOF attenuator utilized on the airplane windshield.
Figure 5B:
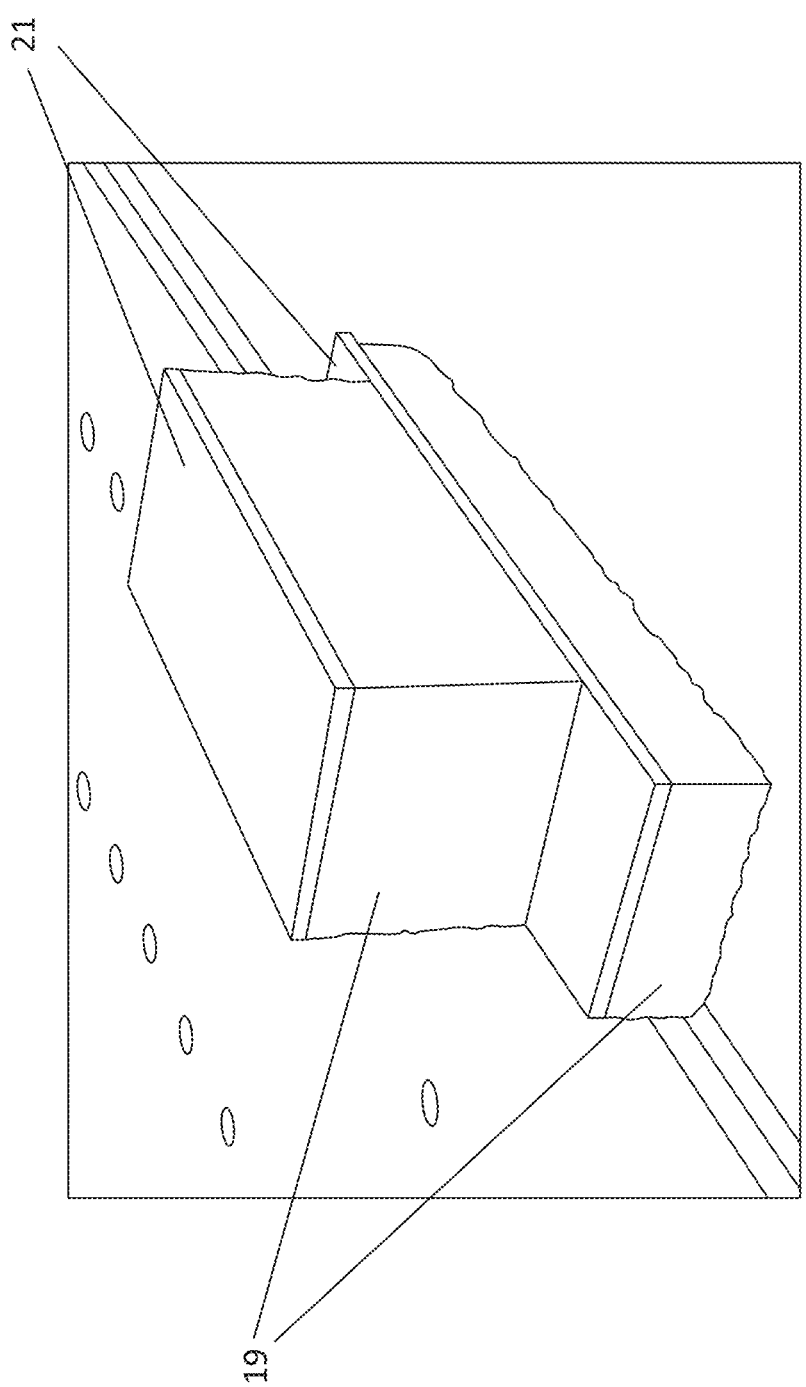
FIG. 5B is a picture of a 2-DOF attenuator system attached to the windshield that is diagramed in FIG. 3.
Figure 6A:
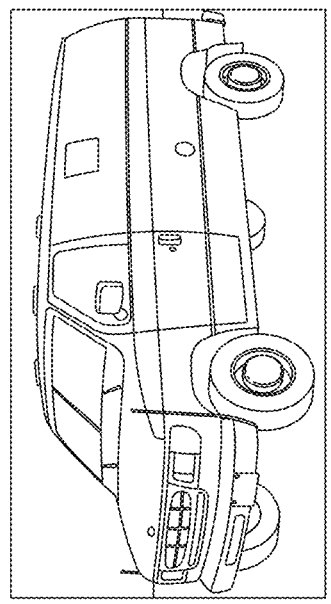
FIGS. 6A-6D are schematic views showing windshields of armored trucks and Piper airplanes which may utilize the novel attenuators of the present invention.
Figure 6B:
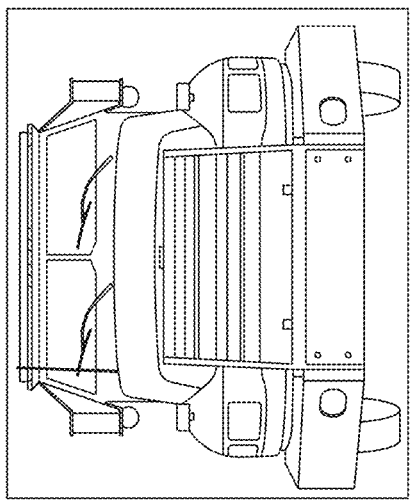
Figure 6C:
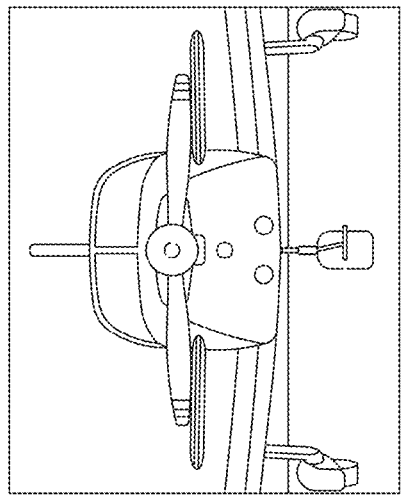
Figure 6D:
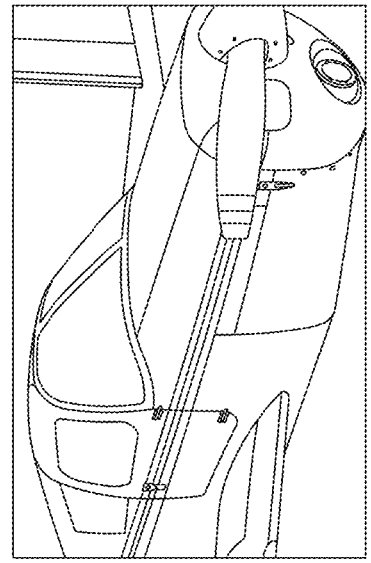

The elastic layer 19 (FIGS. 4A-4C) contains damping and stiffness characteristics and may be formed of foam, gel, sand, rubber, polymer, or any other substance of elastic form. Mass layer 21 may be formed of metal (including steel, aluminum, or any other metal composite), rock, stone, concrete, brick, plastic, or any other material of a fixed, solid state. Mass(es) 21 may be adhered, fastened, bolted, or secured in any similar manner to an elastic layer. Similarly, an elastic layer 19 may be adhered, fastened, bolted, or secured in any similar manner to a surface being attenuated. A model of a 2-DOF attenuator attached to a windshield, can be seen in FIG. 5A. FIG. 5B is a photograph of the concept modeled in FIG. 5A.

In designing an attenuator for the windshield mode at 80-90 Hz, ideally it would be helpful to design the mass of the attenuator to be around 4% of the total mass of the plexiglass. A mass ratio is calculated as shown in Equation 2:

$$\text{Mass Ratio} = \frac{M_{attenuatou}}{M_{structur}} \quad \text{(Equation 2)}$$

A mass ratio that is greater than 4% of the entity being attenuated will begin to cause what is known (to those that are experienced in the field) as splitting of the resonant peak in the windshield into two smaller peaks, e.g., one slightly lower in frequency and one slightly higher in frequency than the initial peak. However, with the novel attenuators of the present invention, the attenuators can be tuned slightly off from one another in order to prevent peaks from occurring on each side of the original resonant peak.

Figure 7:
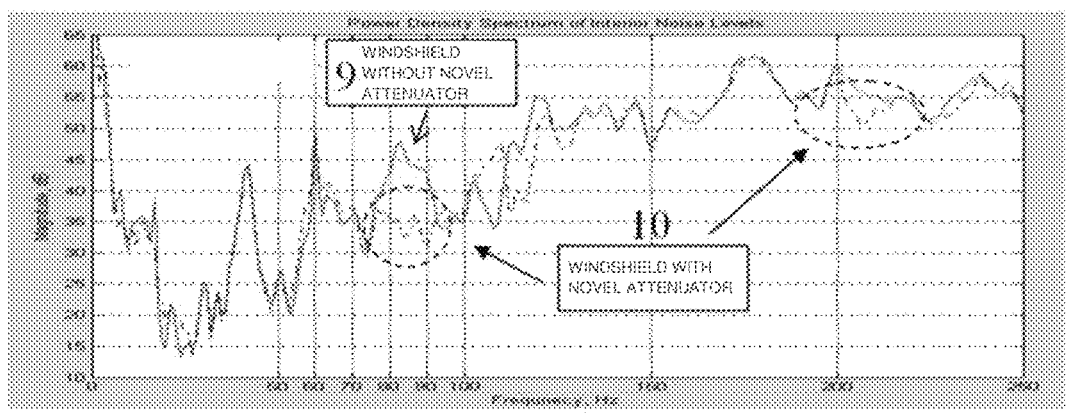
FIG. 7 is a plot of test results, showing sound power levels in the cabin of the fuselage of an airplane with and without a novel attenuator of the present invention. The novel attenuator eliminates energy at two resonant frequencies targeted (e.g., the BPF noise entering the fuselage and a windshield mode that coincides closest to the second harmonic of the BPF)

FIG. 7 shows test results for the sound level in the interior of the airplane fuselage cabin with and without the attenuators (regions 10 and 9, respectively). The attenuators eliminates the resonant peaks at the BPF and 200 Hz windshield mode (regions 10). Even though the mass ratio is above 4%, the staggered attenuation of the attenuators prevents side peaks from occurring, as shown in the area indicated around the 80-90 Hz region.

Figures 8A, 8B:
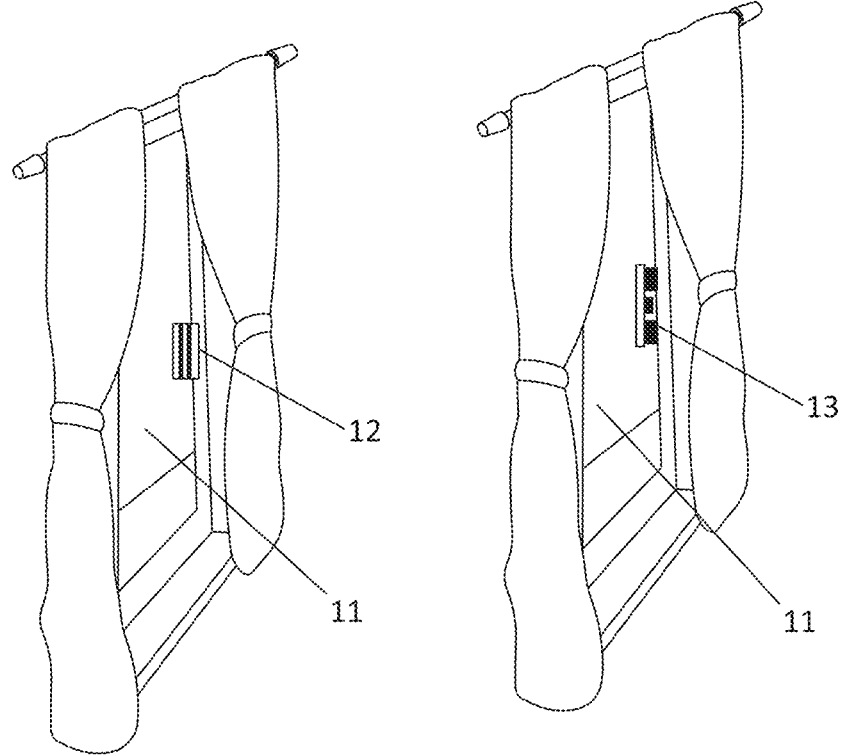
FIG. 8A is a schematic view showing a window utilizing an in-series 3-DOF attenuator.
FIG. 8B is a schematic view showing a window utilizing a parallel 3-DOF attenuator, with variation in mass width, contact surface area, weight, and height.

In another embodiment, and looking now at FIGS. 8A and 8B, an attenuator reduces noise transmission into the interior of a house, building, shopping store, restaurant, library, museum, apartment, or any other similar enclosure. A 3-DOF (in series) attenuator 12 is adhered to a glass structure 11, as shown in FIG. 8A. Similarly, a 3-DOF (in parallel) attenuator 13 is adhered to a glass structure 11, as shown in FIG. 8B.

Figure 9A:
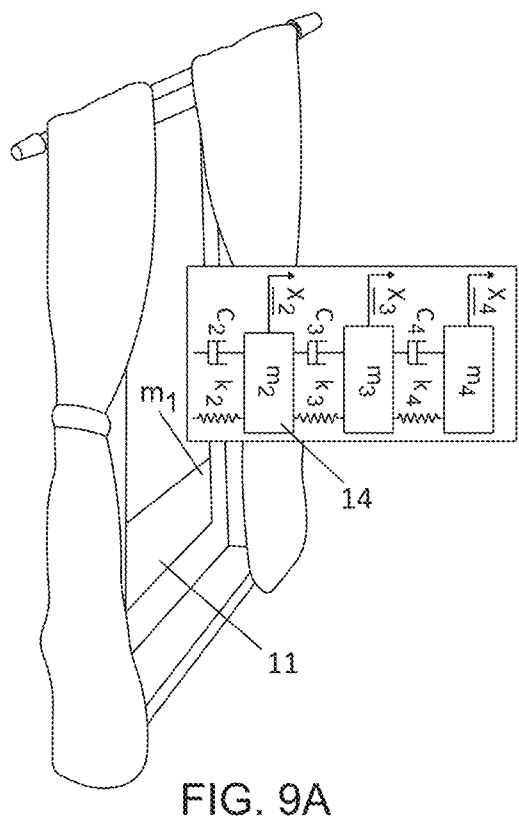
FIG. 9A is a model of the system depicted in FIG. 8A.
Figure 9B:
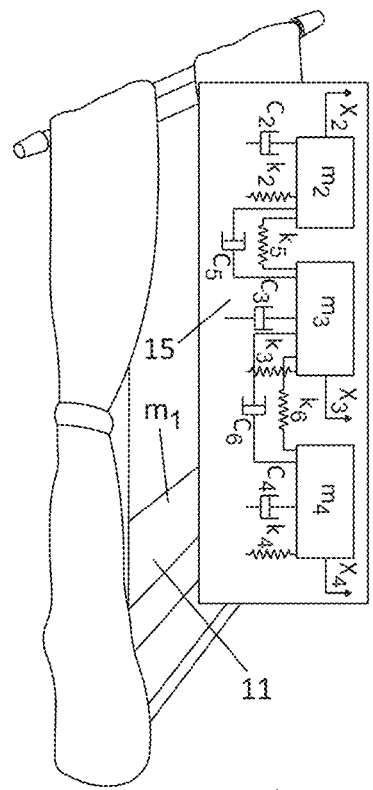
FIG. 9B is a model of the system depicted in FIG. 8B.

A model of the 3-DOF (in series) attenuator shown in FIG. 8A is shown in FIG. 9A (element 14), and a model of the 3-DOF (in parallel) attenuator 13 is shown in FIG. 9B (element 15). The mass of the glass being attenuated is denoted by $m_1$. The stiffness, damping, and mass elements are shown in the model of the attenuator for each DOF.

FIG. 9A shows a model of an in-series attenuator 14, where mass is varied to tune the attenuator to the appropriate peaks of attenuation, and FIG. 9B shows a model of a parallel attenuator 15, where masses with different height, width, weight, and surface contact area are utilized to tune the attenuator to the appropriate peaks of attenuation.

Figure 10:
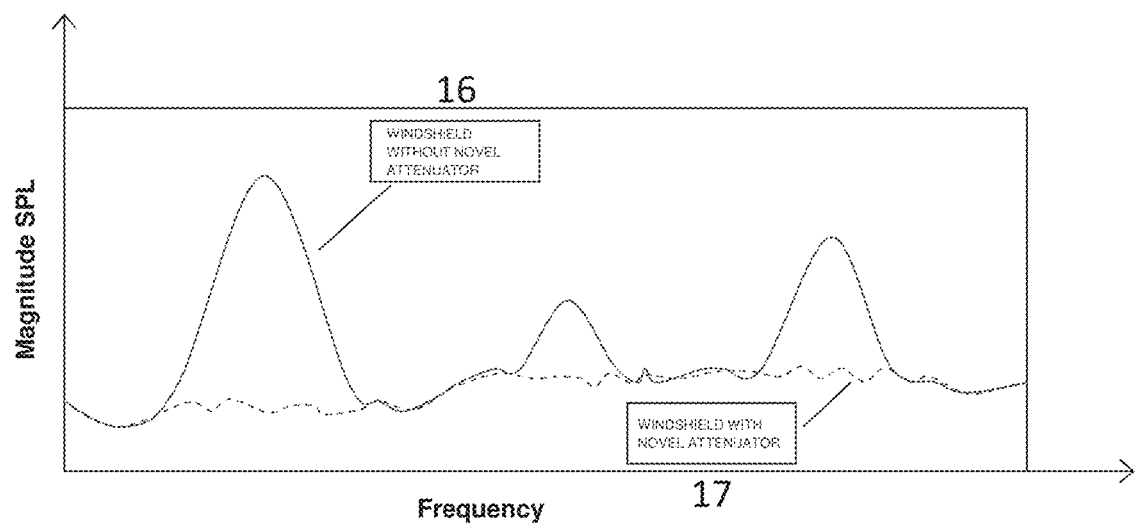
FIG. 10 shows simulated test results of sound levels in the interior of a house with and without a novel attenuator of the present invention—the 3-DOF attenuator can eliminate the acoustical energy at the three resonant peaks entering the house.

Noise transmission through the glass at three distinct resonant peaks is being attenuated by the attenuators shown in FIGS. 9A and 9B (i.e., the attenuators are 3-DOF attenuators). FIG. 10 is a plot showing sound levels inside an enclosure with and without an attenuator being utilized (regions 17 and 16, respectively). The frequency response 17 of the attenuator essentially eliminates the energy at the three resonant peaks.

Figure 11:
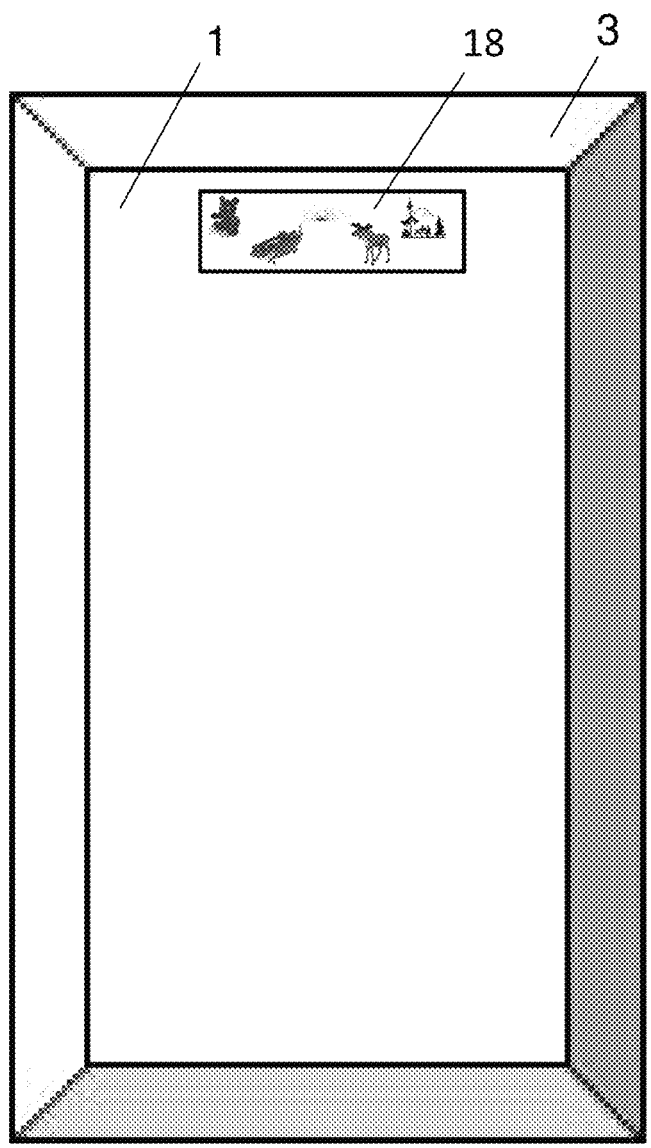
FIG. 11 is a schematic view showing a window equipped with a multi-DOF attenuator, wherein the mass elements of the multi-DOF attenuator are shown in various shapes, sizes, scenes, etc. to enhance the aesthetics of the attenuator for interior decoration—in this particular attenuator, five masses are utilized (i.e., for a 5-DOF attenuator), but it will be appreciated that, theoretically, a lesser or greater number of masses can be utilized to attenuate a smaller or larger number of resonant peaks of noise transmitting through the window into the interior of a house, building, apartment, restaurant, etc.

In a further attenuator embodiment, a multi-DOF attenuator 18 is attached to glass 1, as shown in FIG. 11. The masses of the multi-DOF attenuator 18 can be various sizes, shapes, colors, scenes, forms of artwork, animals, places, and any other design to enhance the décor of a room, store, shop, restaurant, etc. aesthetically. As many DOF systems can be utilized as necessary to attenuate unwanted noise propagating through the glass.

Figure 12:
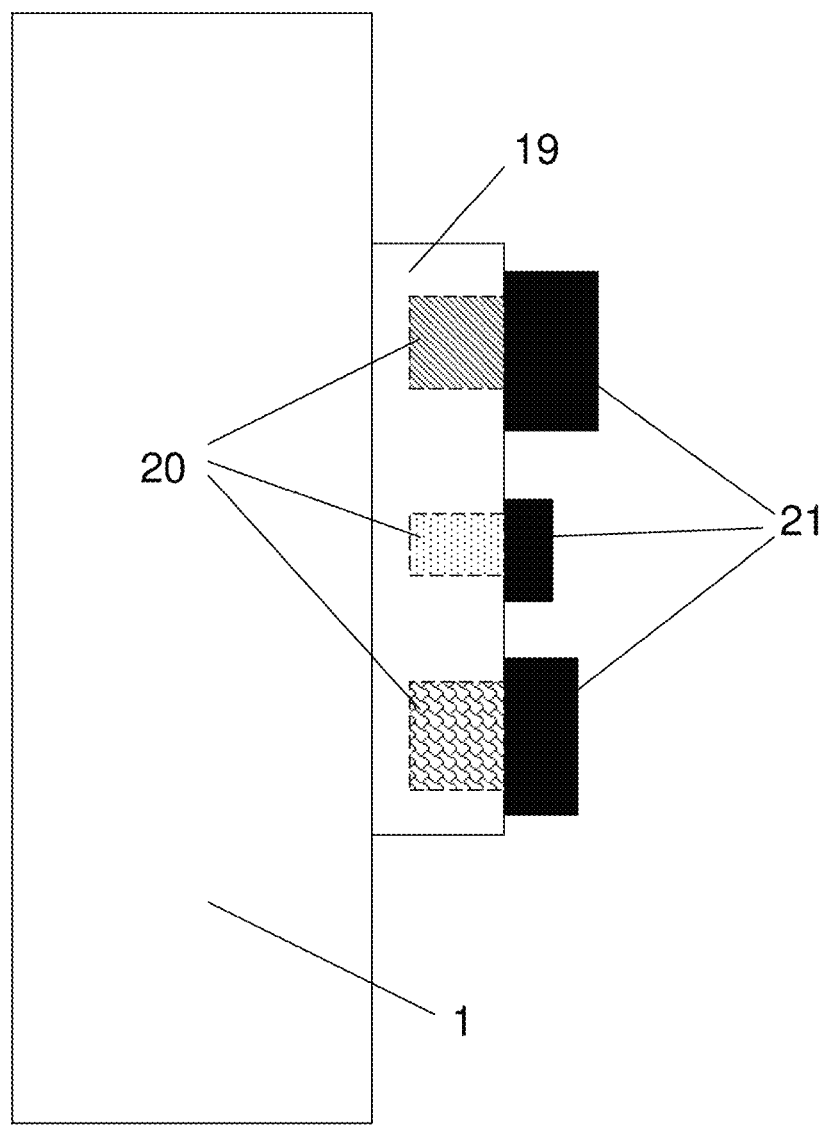
FIG. 12 is a top view (i.e., looking down) of another 3-DOF attenuator formed in accordance with the present invention with chambers bored out in the elastic layer of the attenuator and filled with three distinct materials of solid or liquid (or otherwise flowable) form.

In another preferred embodiment, and looking now at FIG. 12, the attenuator comprises a multi-DOF attenuator (for simplicity, a 3-DOF system is shown in FIG. 12) where holes are bored out of the elastic layer 19 (which could be made out of rubber, foam, gel, or another substance of elastic form). The holes are then filled with a material 20 that is different than the encompassing elastic layer 19. By way of example but not limitation, the elastic layer may be formed of foam and could be bored out and packed with sand, gel, and/or rubber could be placed in the different chambers. Various masses 21 can then be applied on top of the filled chambers (columns). Masses 21 are supported primarily (or entirely) by the filled chambers, although they may also receive some structural support from elastic layer 19.

The different material in each chamber can target a separate attenuation peak in order to cancel unwanted peaks of noise propagating through the glass. Moreover, by adjusting the surface contact area (between the mass and the chamber filled material 20), the peak of attenuation can be increased or decreased.

For instance, keeping mass 21 constant, if the contact area of mass 21 with the filled chamber is decreased, then the attenuation peak decreases. Similarly, if the contact area of mass 21 with the filled chamber increases, then the attenuation peak increases, as related in Equation 3:

$$f_{Attenuation\ Peak} = \frac{\left(\frac{k^* SA}{m}\right)^{1/2}}{2\pi} \quad \text{(Equation 3)}$$

in which SA is the contact surface area of the filled chamber, k is the stiffness of the filled chamber, and m is the mass (which could be of any metal or metal composite, including steel, aluminum, etc., rock, concrete, stone, plastic, or any other solid material). Multiple peaks of noise can then be mitigated by a multiple-DOF attenuator.

Figures 13A, 13B:
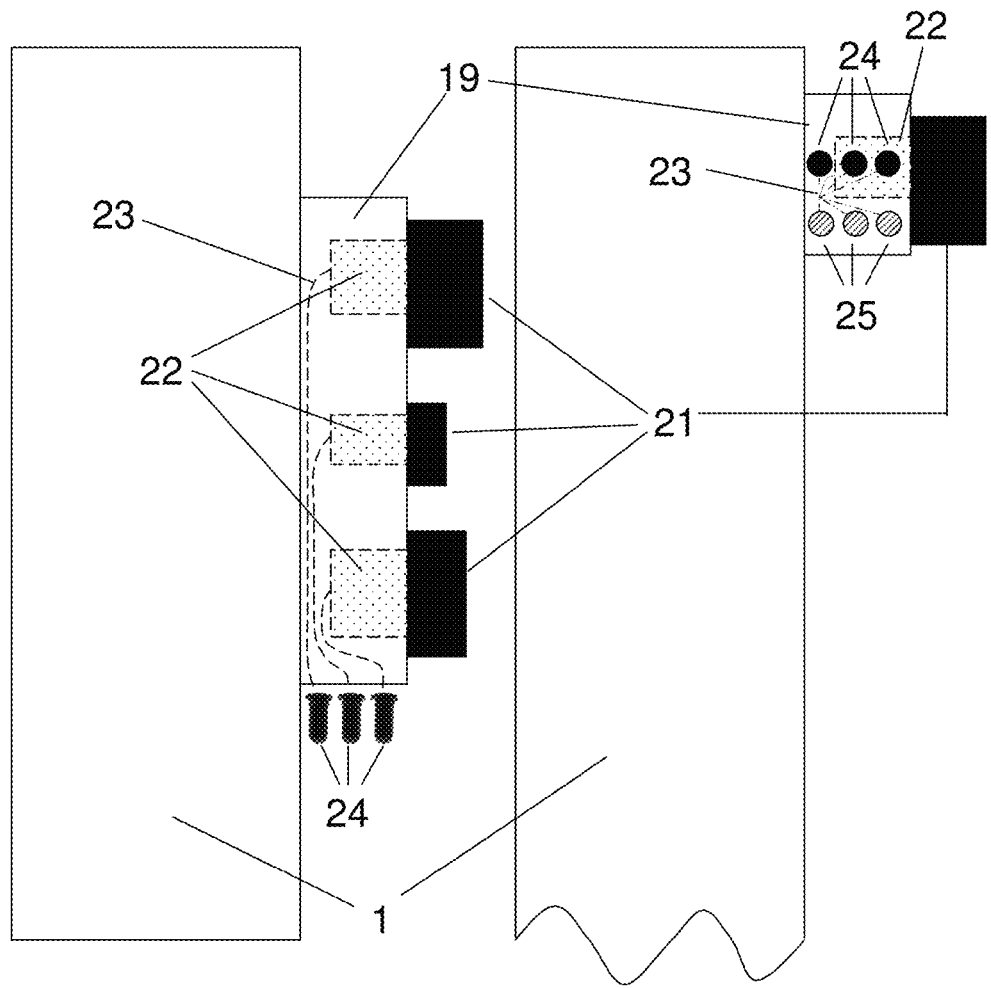

In another preferred embodiment, as shown in FIGS. 13A and 13B, the attenuator utilizes chambers in an elastic layer 19 that is filled with bags/balloons of air and/or any other type of gaseous mixture 22. Plastic tubing 23 from the gas-filled balloon/sacks connect to rubber bulbs 24 placed on the side of the attenuator. By pumping the bulbs, air can be pumped to the balloon in the chamber, thereby increasing the pressure of the filled chamber (column) on which mass 21 is sitting. The change in pressure changes the stiffness of the filled chamber (column), which can shift the attenuation peak. For an increase in pressure, the stiffness increases and the frequency of the attenuation peak increases.

In order to decrease the pressure in the balloon/sack, and thereby decrease the frequency of the attenuation peak, valves/knobs 25 are placed on the side of the attenuator, as shown in FIG. 13B. When valves/knobs are actuated, air is allowed out of the bags.

This enables a user to change the attenuation attributes of the attenuator in order to address a particular environment. By way of example but not limitation, if a house is on a busy street and is constantly being barraged by vehicle engine-noise of around 100 Hz, then the user can adjust one of the attenuators to address the peaks of attenuation to compensate. In another example, if an office building is near an airport and needs to tune an attenuation peak to cancel out a particular airplane BPF at 85 Hz, then the attenuator can be adjusted accordingly.

Figures 14A, 14B:
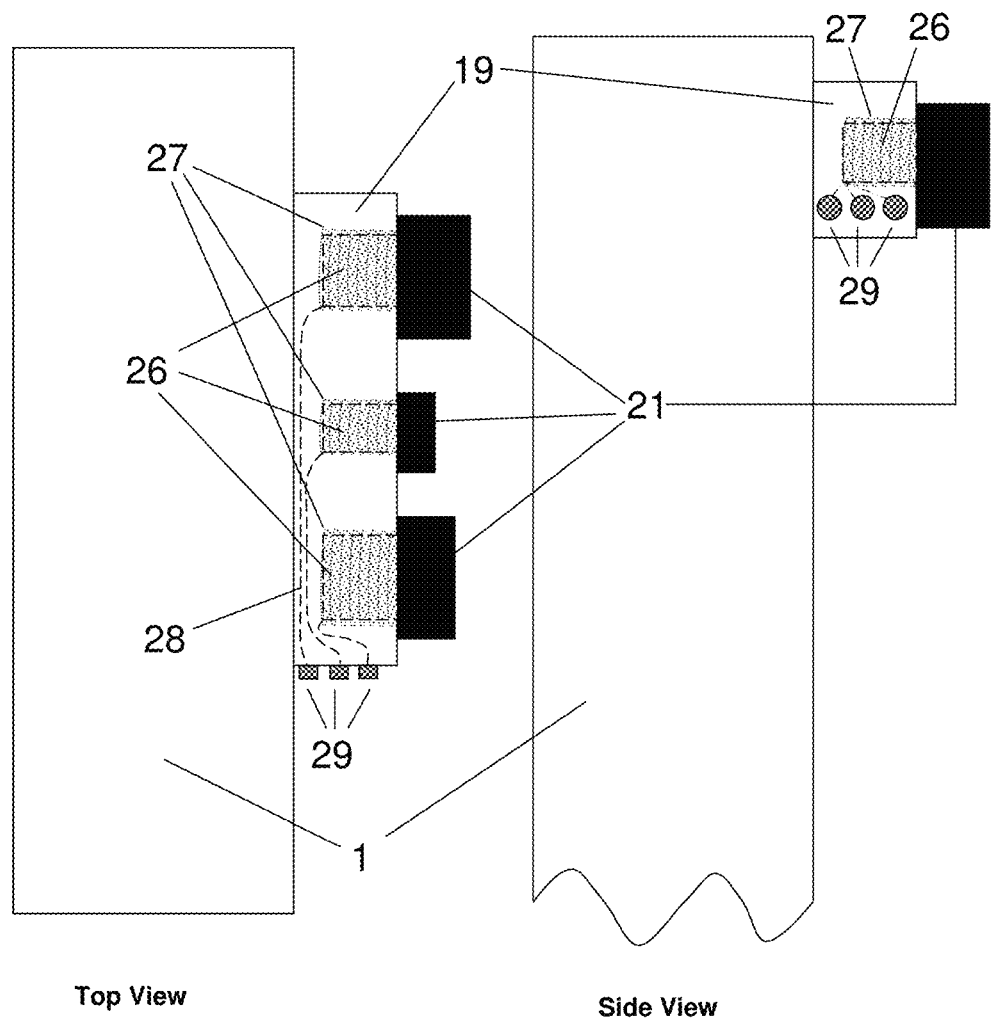
FIGS. 14A and 14B are schematic views showing a novel attenuator that can be adjusted to attenuate varying resonant peaks of noise for a particular environment—the chambers in the elastic layer of the attenuator are filled with a magnetorheological (MR) fluid, coils are wound around the filled chambers, and current is supplied to the coils, creating a magnetic field—the higher the current that is supplied to the coils, the higher the stiffness that is created in the filled chamber (column) to support the mass, whereby to individually adjust the resonant peaks of attenuation to cancel the resonant peaks of noise propagating into the interior of a room, cabin, etc. for a particular environment.

In still another preferred embodiment, and looking now at FIGS. 14A and 14B, an attenuator utilizes chambers in the elastic layer 19, and the balloons/sacks/plastic lining is filled with a high viscosity magnetorheological (MR) fluid 26. Coils 27 are wrapped around the filled chambers (columns) and wires 28 are connected from the coils to knobs 29 on the side of the attenuator.

A low-voltage battery or voltage supply is used to send a small amount of current to a particular coil when a knob is turned. Current flowing through a coil 27 will create a magnetic field, which will stiffen the MR fluid in the filled chamber (column). This in turn will increase the frequency of an attenuation peak, as needed to counteract a particular peak of noise propagating through the glass into the interior of an enclosed area.

In yet another preferred embodiment of the invention, and looking now at FIGS. 15A and 15B, there is shown an enhanced form of the invention previously shown in FIGS. 14A and 14B wherein there is provided a fully active system with many DOFs. In this embodiment of the invention, a microphone 35 is utilized as a control feedback sensor that communicates with a CPU 36. Microphone 35 is configured to detect the various frequencies of sound being transmitted through the window and transmits this information to CPU 36. CPU 36 is configured to then automatically send the appropriate amount of current to one or more of the coils so as to create a magnetic field of appropriate strength so as to change the stiffness of a particular DOF system. As described above, the change in stiffness adjusts an attenuation peak in order to cancel a detrimental resonant peak contributing noise in the interior of an enclosure.

As an additional feature, and looking still at FIGS. 15A and 15B, a digital display 37 (with touchscreen controls) can be included, as an optional feature, so as to allow a user to override the active control feedback loop and manually tune one or more of the DOF systems of the attenuator for a particular attenuation peak.

Figure 16A:
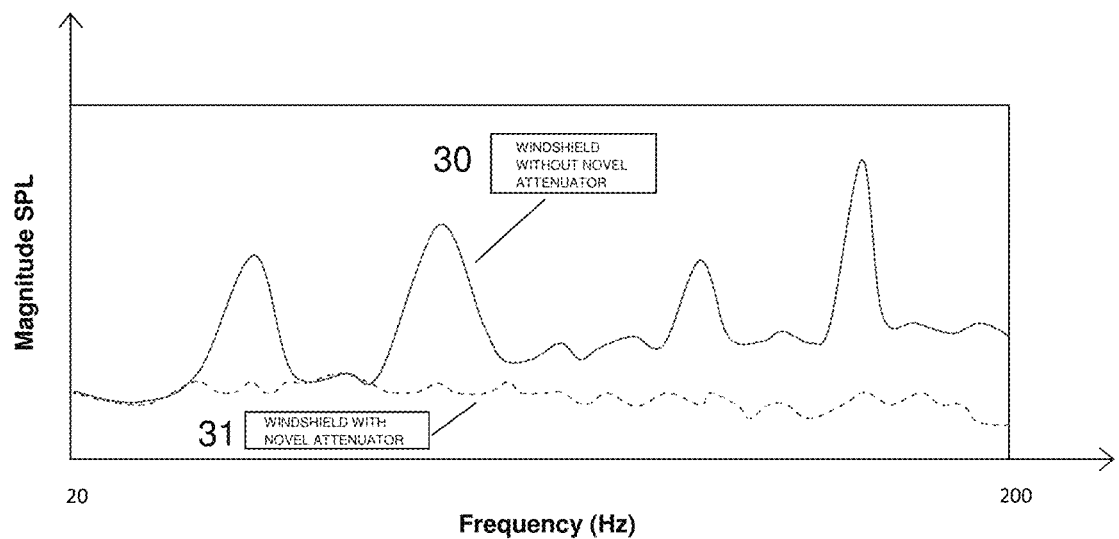
FIGS. 16A and 16B are plots of test results for sound levels in the interior of an enclosure, with and without a multi-DOF attenuator
Figure 16B:
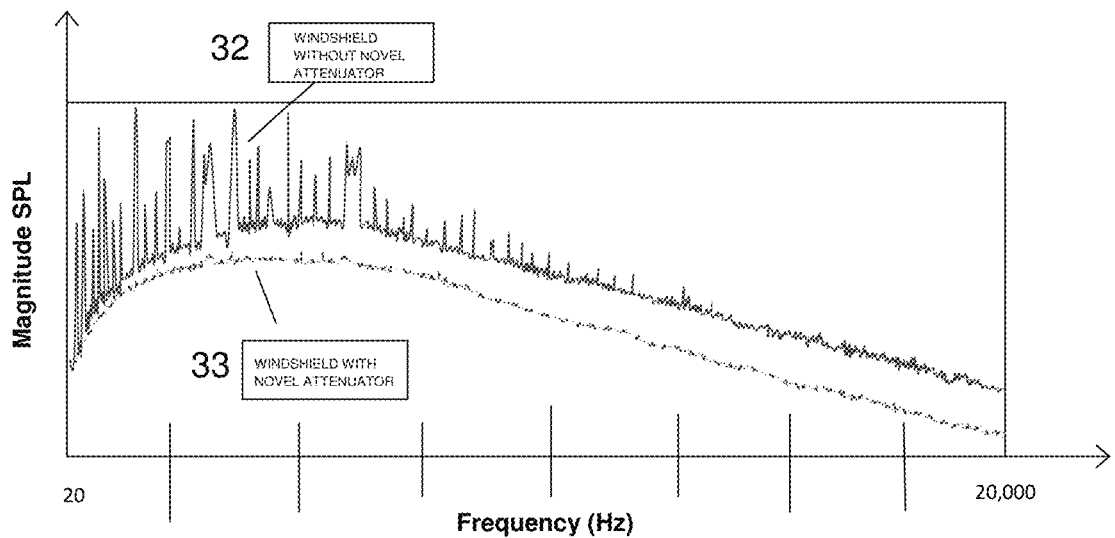

For embodiments of the invention wherein the attenuator has multiple DOF systems, such as the embodiment shown in FIGS. 15A and 15B, many peaks of noise can be attenuated. By way of example but not limitation, FIGS. 16A and 16B shows representative plots in which the attenuator is attenuating many peaks of noise. Peaks can be attenuated for low frequency noise (20 to 200 Hz), as shown in FIG. 16A. Many peaks across the entire human hearing range can also be targeted, as shown in FIG. 16B, to reduce broadband noise propagating through the glass into the interior of an enclosure. An acoustical rating system for windows could then be established, utilizing Table 1, and implemented for particular houses or buildings.

In one aspect of the invention, there is provided a novel attenuator that utilizes an acoustical rating system for the levels of sound propagation through a structure. An acoustical rating system is introduced, as described in Table 1, for the building and construction industry. Just as windows and insulation have an R-value to define the temperature energy efficiency of the interior of a room, the acoustical rating system could define the acoustical energy efficiency of an enclosure space. In the summer, the higher the R-value, the less cool air that escapes a room through a window (and the less heat that penetrates into the interior of the room), thus keeping the room cooler with less energy. Similarly, in the winter, the higher the R-value, the less heat that escapes a room through the window (and the less cool air that penetrates into the interior), thus keeping the room hotter with less energy. In a similar manner, the higher the acoustical rating of a window, the less noise that propagates into the interior of an enclosure, thus maintaining lower levels of sound in the interior of an enclosure, creating a more harmonious, acoustically energy efficient room for enhanced health, preventing sleep interference, speech interference, and maintaining safety levels according to EPA and OSHA standards. An acoustical rating system can help set standards for acceptably attenuated windows for a particular area or jurisdiction for sound quality, especially low frequency noise (e.g. 20 to 200 Hz).

An approach for acoustically rating windows can be seen in Table 1. An A-Rating™ scheme is introduced as well as a S-Rating™ scheme for the sound quality of windows. The A-Rating™ scheme rates windows for low frequency sound from 20-200 Hz while the S-Rating™ scheme rates windows for sound throughout the entire human hearing range of 20-20,000 Hz for the building and construction industry. The majority of noise pollution in the US is due to low frequency noise (due to a long wavelength), which is more difficult and costly to attenuate to produce soothing, healthy, energy efficient levels.

In another aspect of the invention, there is provided a novel attenuator which offers quiet environments, minimizing noise in the interior of enclosures compared to previous devices.

In another aspect of the invention, there is provided a novel system comprising:

(a) glass, window, windshield, plexi-glass, plastic, and any other apparatus that allows visible light to penetrate through; and (b) at least one attenuator comprising mass/spring/damping element(s) for producing peaks of attenuation on the frequency spectrum, according to Equation 3, to counteract peaks of noise propagating through glass, plexi-glass, plastic windows, windshields, or the like, into the interior of a house, building, shopping store, restaurant, vehicle-cabin, fuselage, locomotive/train/subway cabin, apartment, hotel, room, space, airport, library, museum, or any other similar enclosure, wherein the stiffness and damping characteristics are attributes of an elastic layer comprising foam, gel, sand, rubber, polymer, or any other substance of elastic form, and the mass characteristics are attributes of a mass layer comprising a metal, including steel, aluminum, or any other metal composite, rock, stone, concrete, brick, plastic, or any other material of a fixed, solid-state. Optionally, the system further comprises trim(s), as shown in FIGS. 2B, 3, and 6A-6D, which can also contain attenuators. Furthermore, the system optionally comprises a cover over the top of the attenuator(s) to prevent the attenuator(s) from being tampered with. The cover could be in the shape of a dome, square, rectangle, and any other shape necessary to cover the attenuator without coming into contact with the active elements of the attenuator(s). The cover should have enough space to allow for deflection of small distances (e.g., one inch, two inches, three inches, or more depending on the natural vibration measurements of the glass window/windshield).

In another aspect of the invention, there is provided a novel attenuator which comprises a multi-DOF attenuator that can be attached to the glass structure, as shown in FIG. 11. The masses can be in various sizes, shapes, colors, scenes, forms of artwork, animals, places, and any other design to enhance the décor of a room, store, shop, restaurant, etc. aesthetically. As many DOF systems can be utilized as necessary to attenuate unwanted noise propagating through the glass.

In another aspect of the invention, there is provided a novel attenuator which comprises an elastic layer wherein chambers are bored out of the elastic layer in the form of a cylinder, square/rectangular box, or any other volumetric shape. The chambers can then be filled with a different material such as foam, gel, sand, liquid, or any other substance to which a mass can be adhered, fastened, bolted, cemented, secured or placed into communication with in any way to the material. Each filled chamber (column) can have a unique "buoyancy" (with different stiffness characteristics) in order to create peaks of attenuation at different frequencies to cancel peaks of noise propagating through the glass window/windshield. FIG. 12 shows an example of an attenuator with three separate chambers to create three separate attenuation peaks (i.e. FIG. 12 shows a 3-DOF attenuator). Additional chambers (with masses on top) can be created to obtain additional attenuation peaks as needed. Additional attenuators can also be utilized to increase the number of attenuation peaks as well. Attenuators slightly offset a few Hz from each other can help decrease energy splitting of a resonant peak when a mass ratio of greater than 4% is utilized (see Equation 2 for Mass Ratio equation). Two filled chambers (columns) within the same attenuator can be tuned slightly off in frequency as well to help minimize splitting, if needed. For example, multiple attenuators are utilized in the system shown in FIG. 3, which is similar in appearance to some armored truck windshields or Piper airplane windshields. The attenuators were designed to cancel energy propagating through the windshield at the BPF of the airplane, which coincided with a mode in the 80-90 Hz region and a windshield mode that was closest to the second harmonic of the BPF (approximately 200 Hz). Many of the attenuators were slightly offset in the 80-90 Hz region and thus, the frequency response plot shown in FIG. 7 is void of the windshield resonance being split into two smaller peaks in the 80-90 Hz region.

In another aspect of the invention, there is provided a novel attenuator in which the chamber(s) of the attenuator(s) are filled with bags/balloons of air or any other gas mixture and attached to separate distinct masses, as shown in FIGS. 13A and 13B, which comprise:

(a) plastic tubing that goes from the bags/balloons to rubber bulbs on the side of the attenuator;

(b) rubber bulbs that connect to the plastic tubing that can be squeezed to increase the pressure of a particular filled chamber (column) of air/gas-mixture—as the pressure increases, the stiffness increases, which increases the attenuation peak; and (c) knobs that connect to plastic tubing that connect to the chambers of air/gas-mixture—by turning a knob, pressure can be released from a particular bag/balloon of air/gas-mixture in a chamber, which decreases the frequency of the attenuation peak.

The ability to shift attenuation peak(s) enables a user to change the attenuation attributes of the attenuator for a particular environment. If a house is on a busy street, constantly being barraged by vehicle traffic, in which engine-noise around 100 Hz is the primary acoustic energy propagating through the window, then the user can adjust one of the peaks of attenuation to compensate and counteract the noise. Similarly, if an office building is near an airport and needs to tune an attenuation peak to cancel out a particular airplane BPF (e.g. around 85 Hz), then the attenuator can be adjusted accordingly.

In another aspect of the invention, there is provided a novel attenuator such as can be seen in FIGS. 14A and 14B, in which filled chambers (columns) are formed in the elastic layer and:

(a) the chambers are lined with a liner (preferably a plastic liner) and filled with a high viscosity magnetorheological (MR) fluid;

(b) coils are wrapped around the filled chambers (columns);

(c) wires are connected to the coils; and (d) knobs on the side of the attenuator connect to the wires coming from the coil(s) and can increase, decrease, or turn off current being supplied to the coil(s).

A low-voltage battery or voltage supply would be needed for the knobs to be able to increase, decrease, or turn off current to a particular coil when a knob is turned. Current, when flowing through the coil, will create a magnetic field, which can stiffen the MR fluid in the chambers with an increase in current. This in turn will increase the frequency of an attenuation peak, as needed to counteract a particular peak of noise propagating through the glass into the interior of an enclosed area.

In another aspect of the invention, there is provided a novel attenuator with one or more DOFs, each of which is configured to automatically adjust the attenuator for a particular attenuation peak (see FIGS. 15A and 15B). A microphone is utilized as a control feedback sensor, which sends a signal to a CPU. The CPU can then increase, decrease, or turn off current to a particular coil. This can automatically adjust an attenuation peak to counteract a detrimental resonant peak contributing noise in the interior of an enclosure. The control system in a preferred embodiment can attempt to cancel the highest peaks in the 20-200 Hz region first before concentrating on detrimental peak(s) that might be present in higher frequency regions. For other embodiments, any peak could be selected in the human hearing range in any particular order of preference.

For embodiments with many DOF systems, like the one shown in FIGS. 15A and 15B, many peaks of noise can be attenuated, as shown in FIGS. 16A and 16B. Peaks can be attenuated for low frequency noise (20 to 200 Hz), as shown in FIG. 16A. Many peaks across the entire human hearing range can also be targeted, as shown in FIG. 16B to reduce broadband noise propagating through the glass into the interior of an enclosure. A-rated and/or S-rated windows could then be established, utilizing Table 1, and implemented for particular houses or buildings in a particular area.

Thus it will be seen that, in one form of the invention, there is provided an attenuator for reducing sound transmission through a window, the attenuator comprising:

at least one elastic body characterized by a damping attribute and a stiffness attribute; and at least one mass secured to the at least one elastic body;

wherein the at least one elastic body is configured to be secured to the window intermediate the window and the at least one mass;

and further wherein the damping attribute of the at least one elastic body, the stiffness attribute of the at least one elastic body and the at least one mass are selected so as to provide at least one frequency attenuation bandwidth focused on a single resonant peak of sound transmission through the window. With this form of the invention, the attenuator provides one or more frequency attenuation bandwidths each focused on a single resonant peak of sound transmission (i.e., the attenuator may be characterized as a 1-DOF attenuator, a 2-DOF attenuator, a 3-DOF attenuator, etc.). See, for example, FIGS. 4A, 4B, 4C, 5A, 5B, 9A, 9B, 12, 13A, 13B, 14A, 14B, 15A, and 15B.

In one preferred form of the invention, the damping attribute of the at least one elastic body, the stiffness attribute of the at least one elastic body and the at least one mass are selected so as to provide at least two frequency attenuation bandwidths each focused on a single resonant peak of sound transmission through the window. With this form of the invention, the attenuator provides two or more frequency attenuation bandwidths each focused on a single resonant peak of sound transmission (i.e., the attenuator may be characterized as a 2-DOF attenuator, a 3-DOF attenuator, etc.). See, for example, FIGS. 4B, 4C, 5A, 5B, 9A, 9B, 12, 13A, 13B, 14A, 14B, 15A and 15B.

And in one preferred form of the invention, the attenuator comprises a first elastic body characterized by a first damping attribute and a first stiffness attribute, a second elastic body characterized by a second damping attribute and a second stiffness attribute, a first mass and a second mass, wherein the first elastic body is configured to be secured to the window intermediate window and the first mass, and further wherein the second elastic body is configured to be secured to the first mass intermediate the first mass and the second mass. With this form of the invention, the attenuator provides its elastic bodies and masses in series, whereby to provide two or more frequency attenuation bandwidths each focused on a single resonant peak of sound transmission (i.e., the attenuator may be characterized as a 2-DOF attenuator, a 3-DOF attenuator, etc.). See, for example, FIGS. 4B, 4C, 5A, 5B, 9A and 9B.

And in one preferred form of the invention, the attenuator comprises a first elastic body characterized by a first damping attribute and a first stiffness attribute, a second elastic body characterized by a second damping attribute and a second stiffness attribute, and a third elastic body characterized by a third damping attribute and a third stiffness, a first mass, a second mass and a third mass, wherein the first elastic body is configured to be secured to the window intermediate the window and the first mass, second elastic body is configured to be secured to the first mass intermediate the first mass and the second mass, and the third elastic body is configured to be secured to the second mass intermediate the second mass and the third mass. With this form of the invention, the attenuator provides its elastic bodies and masses in series, whereby to provide three or more frequency attenuation bandwidths each focused on a single resonant peak of sound transmission (i.e., the attenuator may be characterized as a 3-DOF attenuator, a 4-DOF attenuator, etc.). See, for example, FIGS. 4C, 9A and 9B.

And in one preferred form of the invention, the attenuator comprises at least one chamber formed in the at least one elastic body, wherein a material is disposed within the at least one chamber. With this form of the invention, the attenuator provides one or more frequency attenuation bandwidths each focused on a single resonant peak of sound transmission (i.e., the attenuator may be characterized as a 1-DOF attenuator, a 2-DOF attenuator, a 3-DOF attenuator, etc.). See, for example, FIGS. 4C, 12, 13A, 13B, 14A, 14B, 15A, and 15B.

And in one preferred form of the invention, the material filling the at least one chamber of the attenuator comprises a fluid, and the attenuator comprises means for varying the quantity of fluid disposed within said chamber, such that the attenuator provides one or more frequency attenuation bandwidths each focused on a single resonant peak of sound transmission (i.e., the attenuator may be characterized as a 1-DOF attenuator, a 2-DOF attenuator, a 3-DOF attenuator, etc.). See, for example, FIGS. 13A and 13B.

And in one preferred form of the invention, the material filling the at least one chamber of the attenuator comprises a magnetorheological (MR) fluid, and the attenuator comprises means for creating a magnetic field around the at least one chamber so as to reduce the flowability of the material filling the at least one chamber, such that the attenuator provides one or more frequency attenuation bandwidths each focused on a single resonant peak of sound transmission (i.e., the attenuator may be characterized as a 1-DOF attenuator, a 2-DOF attenuator, a 3-DOF attenuator, etc.). See, for example, FIGS. 14A and 14B.

And in one preferred form of the invention, a feedback loop control system may be used to automatically adjust the magnetic field around the at least one chamber so as to provide one or more frequency attenuation bandwidths each focused on a single resonant peak of sound transmission (i.e., the attenuator may be characterized as a 1-DOF attenuator, a 2-DOF attenuator, a 3-DOF attenuator, etc.). See, for example, FIGS. 15A and 15B.

And in one preferred form of the invention, there is provided a system for reducing sound transmission through a window, the system comprising:
  a window; and
  an attenuator attached to the window, the attenuator comprising:
    at least one elastic body characterized by a damping attribute and a stiffness attribute; and
    at least one mass secured to the at least one elastic body;
    wherein the at least one elastic body is configured to be secured to the window intermediate the window and the at least one mass;
  and further wherein the damping attribute of the at least one elastic body, the stiffness attribute of the at least one elastic body and the at least one mass are selected so as to provide at least one frequency attenuation bandwidth focused on a single resonant peak of sound transmission through the window. With this form of the invention, the attenuator provides one or more frequency attenuation bandwidths each focused on a single resonant peak of sound transmission (i.e., the attenuator may be characterized as a 1-DOF attenuator, a 2-DOF attenuator, a 3-DOF attenuator, etc.). See, for example, FIGS. 4A, 4B, 4C, 5A, 5B, 9A, 9B, 12, 13A, 13B, 14A, 14B, 15A, and 15B.

And in one preferred form of the invention, there is provided a method for reducing sound transmission through a window, the method comprising:
  attaching an attenuator to the window, the attenuator comprising:
    at least one elastic body characterized by a damping attribute and a stiffness attribute; and
    at least one mass secured to the at least one elastic body;
    wherein the at least one elastic body is configured to be secured to the window intermediate the window and the at least one mass;
  and further wherein the damping attribute of the at least one elastic body, the stiffness attribute of the at least one elastic body and the at least one mass are selected so as to provide at least one frequency attenuation bandwidth focused on a single resonant peak of sound transmission through the window. With this form of the invention, the attenuator provides one or more frequency attenuation bandwidths each focused on a single resonant peak of sound transmission (i.e., the attenuator may be characterized as a 1-DOF attenuator, a 2-DOF attenuator, a 3-DOF attenuator, etc.). See, for example, FIGS. 4A, 4B, 4C, 5A, 5B, 9A, 9B, 12, 13A, 13B, 14A, 14B, 15A, and 15B.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. An attenuator for reducing sound transmission at a selected frequency bandwidth through a window, wherein the window has at least one resonant peak of sound transmission, said attenuator comprising:
    at least one elastic body, said at least one elastic body having at least one chamber formed therein, and said at least one chamber containing contents which may be selectively modified, while said attenuator is mounted to the window and without requiring disassembly of said attenuator, so as to modulate at least one physical property of said contents of said at least one chamber, whereby to modulate the stiffness of said at least one elastic body; and
    at least one mass secured to said at least one elastic body;
    wherein said at least one elastic body is configured to be secured to the window intermediate the window and said at least one mass; and
    at least one tuning element in communication with the contents of said at least one chamber, said at least one tuning element being configured to modify said at least one physical property of said contents of said at least one chamber while said attenuator is mounted to the window and without requiring disassembly of said attenuator, whereby to provide at least one frequency attenuation bandwidth focused on at least one of (i) a selected frequency bandwidth of sound transmission through the window, and (ii) a single resonant peak of sound transmission through the window.

2. An attenuator according to claim 1 wherein said contents of said at least one chamber comprise a fluid.

3. An attenuator according to claim 2 wherein said at least one tuning element is configured to vary the quantity of fluid contained within said at least one chamber.

4. An attenuator according to claim 3 wherein said at least one tuning element comprises at least one reservoir for said contents, at least one tube for carrying said fluid between said at least one reservoir and said at least one chamber, and at least one valve for regulating the flow of fluid between said at least one reservoir and said at least one chamber.

5. An attenuator according to claim 2 wherein said at least one tuning element is configured to vary the flowability of said fluid within said at least one chamber.

6. An attenuator according to claim 5 wherein said at least one tuning element comprises electrical current run through wires disposed in at least one coiled configuration around said at least one chamber so as to create at least one magnetic field within said at least one chamber.

7. An attenuator according to claim 6 wherein said fluid comprises magnetorheological (MR) fluid, and further wherein the creation of at least one magnetic field within said at least one chamber causes the magnetorheological (MR) fluid to have reduced flowability.

8. An attenuator according to claim 2 wherein said fluid comprises a gas.

9. An attenuator according to claim 2 wherein said fluid comprises a liquid.

10. An attenuator according to claim 1 wherein said contents of said at least one chamber comprise a solid.

11. An attenuator according to claim 1 wherein said at least one tuning element comprises a sensor for detecting sound transmission passing through the window to which the attenuator is secured, and a feedback unit for modifying said contents of said at least one chamber so as to modulate at least one physical property of said contents of said at least one chamber in accordance with the sound transmission detected by said sensor.

12. An attenuator according to claim 11 wherein said sensor comprises a microphone.

13. An attenuator according to claim 11 wherein said feedback unit comprises a CPU.

14. An attenuator according to claim 1 wherein said at least one mass is disposed adjacent to said at least one chamber.

15. An attenuator according to claim 14 wherein said at least one mass is aligned with said at least one chamber.

16. An attenuator according to claim 1 wherein said attenuator comprises a plurality of chambers formed in said at least one elastic body, each chamber containing contents which may be selectively modified, while said attenuator is mounted to the window and without requiring disassembly of said attenuator, so as to modulate said at least one physical property of said contents of said plurality of chambers and hence modulate the stiffness of said at least one elastic body, and further wherein said at least one tuning element is in communication with the contents of said plurality of chambers and configured to modify said at least one physical property of said contents of said plurality of chambers while said attenuator is mounted to the window and without requiring disassembly of said attenuator, whereby to provide at least two frequency attenuation bandwidths each focused on at least one of (i) a selected frequency bandwidth of sound transmission through the window, and (ii) a single resonant peak of sound transmission through the window.

17. An attenuator according to claim 16 wherein said plurality of chambers comprise different volumes.

18. An attenuator according to claim 16 wherein said attenuator comprises a plurality of masses secured to said at least one elastic body.

19. An attenuator according to claim 18 wherein a separate mass is provided for each chamber.

20. An attenuator according to claim 19 wherein each mass is disposed adjacent to a chamber.

21. An attenuator according to claim 20 wherein each mass is aligned with a chamber.

22. A system for reducing sound transmission through a window, said system comprising:
    a window; and
    an attenuator attached to said window, said attenuator comprising:
        at least one elastic body, said at least one elastic body having at least one chamber formed therein, and said at least one chamber containing contents which may be selectively modified, while said attenuator is mounted to the window and without requiring disassembly of said attenuator, so as to modulate at least one physical property of said contents of said at least one chamber whereby to modulate the stiffness of said at least one elastic body; and
        at least one mass secured to said at least one elastic body;

wherein said at least one elastic body is configured to be secured to said window intermediate said window and said at least one mass; and at least one tuning element in communication with the contents of said at least one chamber, said at least one tuning element being configured to modify said at least one physical property of said contents of said at least one chamber while said attenuator is mounted to said window and without requiring disassembly of said attenuator, whereby to provide at least one frequency attenuation bandwidth focused on at least one of (i) a selected frequency bandwidth of sound transmission through said window, and (ii) a single resonant peak of sound transmission through said window.

23. A method for reducing sound transmission through a window, said method comprising:

attaching an attenuator to the window, said attenuator comprising:

at least one elastic body, said at least one elastic body having at least one chamber formed therein, and said at least one chamber containing contents which may be selectively modified, while said attenuator is mounted to the window and without requiring disassembly of said attenuator, so as to modulate at least one physical property of said contents of said at least one chamber whereby to modulate the stiffness of said at least one elastic body; and at least one mass secured to said at least one elastic body;

wherein said at least one elastic body is configured to be secured to the window intermediate the window and said at least one mass; and at least one tuning element in communication with the contents of said at least one chamber, said at least one tuning element being configured to modify said at least one physical property of said contents of said at least one chamber while said attenuator is mounted to the window and without requiring disassembly of said attenuator, whereby to provide at least one frequency attenuation bandwidth focused on at least one of (i) a selected frequency bandwidth of sound transmission through the window, and (ii) a single resonant peak of sound transmission through the window; and using said at least one tuning element to modify said at least one physical property of said contents of said at least one chamber while said attenuator is mounted to the window and without disassembly of said attenuator, whereby to provide at least one frequency attenuation bandwidth focused on at least one of (i) a selected frequency bandwidth of sound transmission through the window, and (ii) a single resonant peak of sound transmission through the window.

24. A method according to claim 23 wherein said at least one tuning element comprises a sensor for detecting sound transmission passing through the window to which the attenuator is secured, and a feedback unit for automatically modifying said at least one physical property of said contents of said at least one chamber so as to modulate the stiffness of said contents of said at least one chamber.

25. An acoustic rating system for windows wherein the rating for a given window is a function of the characteristic of the window to transmit sound amplitude and frequency.

26. A method according to claim 25 wherein the acoustic rating system is as defined in Table 1.

27. A method for characterizing a window, the method comprising:

testing the sound transmission of a window; and characterizing the window in the context of an acoustic rating system wherein the rating for a given window is a function of the characteristic of the window to transmit sound amplitude and frequency.

* * * * *